United States Patent
Hyeon et al.

(10) Patent No.: US 8,871,310 B2
(45) Date of Patent: Oct. 28, 2014

(54) SURFACE-MODIFIED TANTALUM OXIDE NANOPARTICLES, PREPARATION METHOD THEREOF, AND CONTRAST MEDIUM FOR X-RAY COMPUTED TOMOGRAPHY AND HIGHLY DIELECTRIC THIN FILM USING SAME

(75) Inventors: Taeghwan Hyeon, Seoul (KR); Myoung Hwan Oh, Seoul (KR)

(73) Assignee: SNU R&DB Foundation, Seoul (KR)

( * ) Notice: Subject to any disclaimer, the term of this patent is extended or adjusted under 35 U.S.C. 154(b) by 0 days.

(21) Appl. No.: 13/580,594

(22) PCT Filed: Feb. 22, 2011

(86) PCT No.: PCT/KR2011/001165
§ 371 (c)(1),
(2), (4) Date: Nov. 5, 2012

(87) PCT Pub. No.: WO2011/105736
PCT Pub. Date: Sep. 1, 2011

(65) Prior Publication Data
US 2013/0065995 A1 Mar. 14, 2013

(30) Foreign Application Priority Data
Feb. 23, 2010 (KR) .................. 10-2010-0016365

(51) Int. Cl.
*B05D 1/30* (2006.01)
*A61K 49/04* (2006.01)
*B82Y 5/00* (2011.01)

(52) U.S. Cl.
CPC .............. *A61K 49/0428* (2013.01); *B82Y 5/00* (2013.01)
USPC ........ 427/443.1; 427/220; 523/213; 524/408; 524/430

(58) Field of Classification Search
USPC ......... 524/408, 430; 427/220, 443.1; 523/213
See application file for complete search history.

(56) References Cited

U.S. PATENT DOCUMENTS
6,696,585 B1    2/2004   Wellinghoff et al.

FOREIGN PATENT DOCUMENTS
KR  10-2009-0108697      * 10/2009
WO  WO 2006/123937 A2   11/2006
WO  WO 2008/092059 A2    7/2008

OTHER PUBLICATIONS

Kishida, M., et. al., "Preparation of Silica-Coated Rhodium Nanoparticles Using Water-in-Oil Microemulsion", Chemistry Letters, 2000, vol. 29, No. 9, pp. 1108-1109.
Holzinger, D., et al., "Preparation of Amorphous Metal-Oxide-Core Polymer-Shell Nanoparticles via a Microemulsion-Based Sol-Gel Approach", Chemistry of Materials, 2003, vol. 15, pp. 4944-4948.
International Search Report issued in International Application No. PCT/KR2011/001165 on Nov. 30, 2011.

* cited by examiner

*Primary Examiner* — Peter Szekely
(74) *Attorney, Agent, or Firm* — Hoffmann & Baron, LLP

(57) ABSTRACT

The present invention relates to a surface-modified tantalum oxide nanoparticle, a method for preparation thereof, a contrast agent (medium) for X-ray computed tomography, and a highly dielectric (high-κ) film using the same. In particular, the present invention is directed to a surface-modified tantalum oxide nanoparticle, a method for preparing surface-modified tantalum oxide nanoparticles, comprising: (i) adding an aqueous phase to an organic solvent which contains a surfactant, to prepare a water-in-oil microemulsion; (ii) introducing a tantalum precursor to said microemulsion; (iii) adding a surface-modifier having an organic silane group or phosphine group to a solution obtained at the step (ii); (iv) removing said organic solvent from a product obtained at the step (iii); and (v) separating surface-modified tantalum oxide nanoparticles from a mixture obtained at the step (iv), a contrast agent for X-ray computed tomography, and a highly dielectric (thin) film using the same.

33 Claims, 23 Drawing Sheets

SURFACE-MODIFIED TANTALUM OXIDE NANOPARTICLES, PREPARATION METHOD THEREOF, AND CONTRAST MEDIUM FOR X-RAY COMPUTED TOMOGRAPHY AND HIGHLY DIELECTRIC THIN FILM USING SAME

This application is the U.S. National Phase of, and Applicants claim priority from, International Application Number PCT/KR2011/001165 filed Feb. 22, 2011 and Korean Patent Application No. KR 10-2010-0016365 filed Feb. 23, 2010, each of which are incorporated herein by reference.

TECHNICAL FIELD

The present invention relates to a surface-modified tantalum oxide nanoparticle, a method for preparation thereof, a contrast agent (medium) for X-ray computed tomography, and a highly dielectric (high-κ) film using the same. In particular, the present invention is directed to a surface-modified tantalum oxide nanoparticle, a method for preparing surface-modified tantalum oxide nanoparticles, comprising: (i) adding an aqueous phase to an organic solvent which contains a surfactant, to prepare a water-in-oil microemulsion; (ii) introducing a tantalum precursor to said microemulsion; (iii) adding a surface-modifier having an organic silane group or phosphine group to a solution obtained at the step (ii); (iv) removing said organic solvent from a product obtained at the step (iii); and (v) separating surface-modified tantalum oxide nanoparticles from a mixture obtained at the step (iv), a contrast agent for X-ray computed tomography, and a highly dielectric (thin) film using the same.

BACKGROUND ART

For the past decades, nanomaterials have been attracted for their excellent properties to overcome many difficulties in various research fields. Nano-engineering has a potential in a wide range of applications, including energy storage and transformation, display devices, biomedical imaging and other bio-related applications, data storage media, sensors and other electronic devices, and catalysts.

Recently, researchers have been interested in nanometer-sized tantalum oxide due to their unique properties. For example, tantalum oxide has a better electrical insulation capability, comparing with silica, and is considered as a good candidate for highly dielectric material. In addition, tantalum oxide is ideal material for an anti-reflective coating, a water-splitting catalyst, a fixed metal oxide catalyst and an X-ray contrast agent, due to its high refractive index, thermal and chemical stability, catalytic activity, radiopacity and biocompatibility.

Synthesis and application of tantalum oxide nanoparticles are very important. Nanoparticles with high uniformity and excellent dispersibility in many solvents are required to produce solution-processed electronic and optical devices. Synthesis of mono-disperse nanoparticles capped with suitable stabilizing molecules make it possible to prepare a defect-free film comprised of nanoparticle layers. Moreover, it is very important in a biomedicinal field to developing an easy surface-modifying process. For these purposes, the surface of a nanoparticle should be modified to have functional moieties including antifouling agents, drugs, organic dyes and antibodies, which give colloidal dispersibility and multi-functionality to the nanoparticle.

Meanwhile, derivatives of iodobenzoic acid have been used as X-ray CT contrast agents until now, in spite of their danger and side effects due to iodide. However, it is known that the derivatives of iodobenzoic acid have low molecular weight and are rapidly excreted via renal elimination, resulting in short circulation time that limits their applications for targeting lesions. In addition, many patents disclose the use of gold nanoparticles for X-ray CT contrast agents. However, these gold nanoparticles are not economical. WO 2008/092059 (Korean Patent Application Publication No. 10-2009-0108697) discloses an X-ray CT contrast agent using tantalum oxide nanoparticles. However, there has not yet been any report on surface-modified mono-disperse tantalum oxide nanoparticles, method for simple and low-cost large-scale production thereof and uses of the same.

DISCLOSURE

Technical Problem

The primary object of the present invention is to provide a method for preparing surface-modified tantalum oxide nanoparticles, comprising: (i) adding an aqueous phase to an organic solvent which contains a surfactant, to prepare a water-in-oil microemulsion; (ii) introducing a tantalum precursor to said microemulsion; (iii) adding a surface-modifier having an organic silane group or phosphine group to a solution obtained at the step (ii); (iv) removing said organic solvent from a product obtained at the step (iii); and (v) separating surface-modified tantalum oxide nanoparticles from a mixture obtained at the step (iv).

Another object of the present invention is to provide a surface-modified tantalum oxide nanoparticle comprising a tantalum oxide nanoparticle, and a functional material attached to said tantalum oxide nanoparticle through a phosphine group or a silane group.

Yet another object of the present invention is to provide a contrast agent for X-ray computed totmography comprising a tantalum oxide nanoparticle, and a functional substance which is attached to said tantalum oxide nanoparticle through a phosphine or silane group.

Further object of the present invention is to provide a method for preparing a surface-modified tantalum oxide nanoparticle/polymer nanocomposition, comprising: (i) adding an aqueous phase to an organic solvent which contains a surfactant, to prepare a water-in-oil microemulsion; (ii) introducing a tantalum precursor to said microemulsion; (iii) adding a surface-modifier having an organic silane group or phosphine group to a solution obtained at the step (ii); (iv) removing said organic solvent from a product obtained at the step (iii); (v) separating surface-modified tantalum oxide nanoparticles from a mixture obtained at the step (iv); and (vi) adding said surface-modified tantalum oxide nanoparticle to a solution containing a polymer, followed by heating the thus obtained mixture to remove said solvent, and a highly (high-κ) dielectric film prepared by a method comprising applying the surface-modified tantalum oxide nanoparticle/polymer nanocomposition on a substrate.

Technical Solution

Although all the terms used herein would be understood by one of ordinary skill in the art, the following definitions are provided for understanding the present invention. Unless defined otherwise, all technical and scientific terms herein have the same meaning as commonly understood by one of ordinary skill in the art.

As used herein, the term "X-ray computed tomography (CT)", also known as computed axial tomography (CAT), or body section roentgenography, refers to a medical imaging procedure that utilizes computer-processed X-rays to produce tomographic images of specific areas of the body. Digital geometry processing is used to generate a three-dimensional image of the inside of an object from a large series of two-dimensional X-ray images taken around a single axis of rotation. In spite of focusing on computed tomography herein, a person skilled in the art will recognize that the present invention may be generally applied to all types of X-ray imaging.

As used herein, the term "contrast agent for X-ray computed tomography" refers to an agent that includes a substance which significantly attenuates X-rays transmitted through a volume of interest. After modification of CT images and common post-processing thereof, these enhanced X-ray attenuation is recognized as a density increase of the volume of interest, which produces contrast images of the volume containing the contrast agent, comparing with background tissues. The contrast agent for X-ray computed tomography of the present invention is applicable to all types of X-ray imaging.

As used herein, the term "nanoparticle" refers to particles that have a size of about 1 nm to about 1,000 nm, or have an average size of about 1 nm to about 500 nm. Nanoparticles may include functional groups attached to the surface of the nanoparticles. Shapes of these nanoparticles may be spherical or irregular.

As used herein, the term "microemulsion (ME) method" refers to a method that utilizes water droplets, as microreactors, in an emulsion in order to synthesize nanoparticles. For example, various water-in-oil ME systems utilizing non-ionic surfactants have been used to synthesize mono-disperse silica nanoparticles. In these systems, surfactant molecules form micelles at the interface between an oil phase and a water phase. Under controlled conditions, micelle spheres of a size of less than or equal to about 10 nm may be produced. These micelle spheres may exchange their contents one another by collision. Metal alkoxide precursors and acid/base catalysts exist in an aqueous phase of the inside of each micelle sphere. During synthesis of nanoparticles, metal oxides are formed by hydrolysis and condensation of the precursors, which is known as a sol-gel reaction. Sol-gel reactions inside uniform spherical micelles may lead formation of mono-disperse metal oxide nanoparticles. Micelles may prevent the nanoparticles from aggregation and protect their surface, as well as serve as a soft template.

The size distribution and aggregation rate of the nanoparticles mainly depend on the ratio between the reaction rate of the precursor and the exchange rate of the micelle contents. The growth dynamics of the nanoparticles may be controlled by adjusting pH, concentrations of electrolytes, surfactants and precursors, and ratio of water and oil phase.

It is one of advantages of the ME method that the size and structure of the nanoparticles may be easily controlled by adjusting the ratio of the surfactant and the water. Additionally, core-shell structured nanoparticles may be formed by adding further precursor to the microemulsion system and, then, the core particles may cause reverse micelle swelling.

In the meantime, according to the conventional ME method that, when the nanoparticles are left from the reverse micelle template in order to disperse the nanoparticles into other solvent or to obtain the nanoparticle as powders, the surface of the nanoparticles became unstable and the nanoparticles aggregate. Accordingly, the dispersibility of the nanoparticles should be maintained even when removing the reverse micelles, by introducing a stabilizing agent being attached to the surface of the nanoparticles. Therefore, another stabilizing agent should be introduced continuously, with maintaining the reverse micelle template.

The tantalum oxide nanoparticles of the present invention strongly rely on the strength of the reverse micelle template, due to their highly reactive surfaces. Therefore, the nanoparticles aggregate owing to the weak membrane of the reverse micelle even though other solvent with different solubility of the nanoparticles is added to precipitate the particles for the purpose of purification of the nanoparticles, or the ME system is heated in order to evaporate the solvent of the ME. Accordingly, a method for inducing a covalent bonding between the nanoparticles and the stabilizing agent is used by introduction of a stabilizing agent with or without functional groups. This modifying technique is simple and widely applicable by introduction of stabilizing agents with various functional groups. In addition, the modifying technique makes it easier to purify the nanoparticles, and to produce the nanoparticles in a large scale by recycling the solvent used for the microemulsion.

Highly (high-$\kappa$) dielectric layer plays an important role in enhancing the mobility of electrons of the organic thin film transistor (OTFT), etc. For the better performance of the OTFT, dielectric substance should have high insulation capability, transparency, flexibility and thinness. However, an organic dielectric film has low dielectric constant ($\kappa$=5~10), whereas an inorganic dielectric film is not adhesive to a hydrophobic organic film and needs a high temperature process of melting the organic film in order to attach the inorganic dielectric film to the organic dielectric film. The amorphous tantalum oxide ($TaO_x$) nanoparticles used in the present invention are highly dielectric ($\kappa$~25) and transparent. Further, a colloidal nanoparticle solution may be utilized for solution-based production of a high dielectric film for OTFT, which is cost-effective and suitable for a low temperature process. Therefore, the dielectric film made of $TaO_x$ solution may overcome the disadvantages of the organic dielectric film and the inorganic dielectric film. According to the present invention, tantalum oxide ($TaO_x$, $0<x\leq2.5$) includes $TaO$, $TaO_2$ and $Ta_2O_5$.

Tantalum oxide ($TaO_x$) nanoparticles may be appropriate to an X-ray contrast agent. Recently, gold nanoparticles have drawn attention to an X-ray CT contrast agent due to its prolonged circulation time, high absorption of X-ray, biocompatibility and various modification techniques. However, the properties of tantalum oxide nanoparticles are equal or superior to those of gold nanoparticles. Tantalum has been known as biocompatible material, such as adsorbents and fillers for dental use. Amorphous tantalum oxide has low surface energy, which allows the amorphous tantalum oxide to be biologically compatible with blood. In addition, tantalum oxide has not been reported to be cytotoxic, and is one of the most biocompatible metal-based materials such that tantalum oxide is almost equal to silica and gold in respect of cytotoxicity as a metal-based X-ray contrast agent. Moreover, tantalum is two hundred times cheaper than gold while possessing a comparable X-ray attenuation coefficient (Ta: 4.3 and Au: 5.16 $cm^2$/kg at 100 eV). The tantalum oxide nanoparticles of the present invention may solve the disadvantages which conventional iodinated compounds used as an X-ray contrast agent have. Iodinated compound-based X-ray contrast agents, due to their low X-ray absorption ability, should be used as highly concentrated solutions and, thus, should be administered as highly viscous solutions. In addition, iodinated compounds are readily excreted via renal elimination, resulting in short circulation time and have side effects, for example, anaphylactoid reaction and contrast-induced nephropathy. In the previous study, it had been observed that an X-ray contrast agent which is bonded with an anti-fouling agent and has a high electron density, has a long circulation time and shows higher contrast effects per unit concentration.

The primary object of the present invention can be achieved by providing a method for preparing surface-modified tantalum oxide nanoparticles, comprising: (i) adding an aqueous phase to an organic solvent which contains a surfactant, to prepare a water-in-oil microemulsion; (ii) introducing a tantalum precursor to said microemulsion; (iii) adding a surface-modifier having an organic silane group or phosphine group to a solution obtained at the step (ii); (iv) removing said organic solvent from a product obtained at the step (iii); and (v) separating surface-modified tantalum oxide nanoparticles from a mixture obtained at the step (iv).

The surfactant may be a non-ionic surfactant. In addition, the non-ionic surfactant may be polyoxyethylene-5-nonylphenyl ether (NP-5), polyoxyethylene sorbitan (Tween), poloxamer, sorbitan ester (Span) or combinations thereof.

The organic solvent may be conventional organic solvents that may be used as an organic phase in a microemulsion. More particularly, the organic solvent may be cyclohexane, hexane, heptane, octane, isooctane, nonane, decane, toluene or combinations thereof.

The aqueous phase may further comprise a hydrophilic solvent. The size of tantalum oxide nanoparticles may be controlled by changing the ratio of the water and the hydrophilic solvent. As the amount of the hydrophilic solvent increases, the size of the tantalum oxide nanoparticle increases. Preferably, the hydrophilic solvent may be selected from $C_{1-8}$ alcohol, acetonitrile, $C_{1-8}$ ether or acetone. More preferably, the hydrophilic solvent may be ethanol.

In addition, the aqueous phase may further comprise a co-surfactant such as fatty acid salts. The fatty acid salts may be calcium salt, magnesium salt, potassium salt, etc. of fatty acids and the fatty acids may be saturated or unsaturated. Preferably, the fatty acid salt may be sodium oleate.

Moreover, the aqueous phase may further comprise an acid or a base as a catalyst. Accordingly, the pH of the aqueous phase may be less than or equal to 2, or more than or equal to 13. For example, sodium hydroxide, potassium hydroxide, etc. may be used as a base catalyst and hydrochloric acid, acetic acid, etc. may be used as an acid catalyst.

The tantalum precursor may be tantalum alkoxides or tantalum salts. More preferably, the tantalum precursor may be $C_1$-$C_4$ tantalum alkoxide. Most preferably, the tantalum precursor may be tantalum ethoxide.

The surface modifier may be a silane or phosphine group containing compound, and, preferably, trioctylphosphine (TOP), methacryloxypropyltrimethoxy silane (MPTMS), poly(ethylene glycol) silane, 3-aminopropyltriethoxy silane (APS), tetraethylorthosilicate (TEOS) or combinations thereof. The surface modifier endows the nanoparticle with surface-modifying effects, as well as stabilization effects.

Moreover, the surface-modifier may be a functional substance selected from a biocompatible material, an organic dye, a bioactive material, a functional group, an organic molecule, an organometal, a nanoparticle, a shell structured material or combinations thereof, which is attached to the surface-modifier at the opposite side to a silane or phosphine attached to a surface of the nanoparticle. The functional substance may be any substance that can be attached to the surface of the tantalum oxide nanoparticle having a silane or phosphine group and be added to the reaction of tantalum oxide nanoparticle synthesis.

The biocompatible material may be polyvinyl alcohol, polylactide, polyglycolide, poly(lactide-co-glycolide), polyanhydride, polyester, polyetherester, polycaprolactone, polyesteramide, polyacrylate, polyurethane, polyvinyl fluoride, poly(vinyl imidazole), chlorosulphonate polyolefin, polyethylene oxide, poly(ethylene glycol), dextran, a mixture thereof, or a copolymer thereof.

In addition, the organic dye may be rhodamine, a rhodamine derivative, fluoresceine, a fluoresceine derivative, luciferin, a luciferin derivative or combinations thereof. For example, rhodamine B isothiocyanate (RITC) may be used as the organic dye, according to the present invention.

Further, the bioactive material may be a target-specific material selected from a protein, RNA, DNA, an antibody or combinations thereof, which attaches specifically to an in vivo targeted material; an apoptosis-inducing gene or a toxic protein; a fluorescent material; an isotope; a material responsive to a light, an electromagnetic wave, or heat; a pharmacologically active material; or combinations thereof. According the method of the present invention, the step (iv) may be carried out by heating the organic solvent less than or equal to 60° C. In addition, the organic solvent may be heated equal to or more than its boiling point in the step (iv).

The step (iv) of the method of the present invention may be performed by conventional purification/separation method. For example, the nanoparticles prepared may be purified and separated by solvent-nonsolvent method and centrifugation but not limited thereto.

The method of the present invention may be carried out in a single reactor (one pot), but not limited thereto.

Another object of the present invention can be achieved by providing a surface-modified tantalum oxide nanoparticle comprising a tantalum oxide nanoparticle, and a functional material attached to said tantalum oxide nanoparticle through a phosphine group or a silane group.

The functional material may be selected from a biocompatible material, an organic dye, a bioactive material, a functional group, an organic molecule, an organometal, a nanoparticle, a shell structured material or combinations thereof.

The size of surface-modified tantalum oxide nanoparticle may be 3 nm to 50 nm and the standard deviation of the size is less than or equal to about 5%. The surface-modified tantalum oxide nanoparticle may be TaO.

Yet another object of the present invention can be achieved by providing a contrast agent for X-ray computed totmography comprising a tantalum oxide nanoparticle, and a functional substance which is attached to said tantalum oxide nanoparticle through a phosphine or silane group.

The biocompatible material may be polyvinyl alcohol, polylactide, polyglycolide, poly(lactide-co-glycolide), polyanhydride, polyester, polyetherester, polycaprolactone, polyesteramide, polyacrylate, polyurethane, polyvinyl fluoride, poly(vinyl imidazole), chlorosulphonate polyolefin, polyethylene oxide, poly(ethylene glycol), dextran, a mixture thereof, or a copolymer thereof.

In addition, the organic dye may be rhodamine, a rhodamine derivative, fluoresceine, a fluoresceine derivative, luciferin, a luciferin derivative or combinations thereof. For example, rhodamine B isothiocyanate (RITC) may be used as the organic dye.

The contrast agent for X-ray computed totmography, according to the present invention, may further comprise an organic dye which is attached to the surface of said tantalum oxide nanoparticle through a phosphine or silane group. The bioactive material may be a target-specific material selected from a protein, RNA, DNA, an antibody or combinations thereof, which attaches specifically to an in vivo targeted material; an apoptosis-inducing gene or a toxic protein; a fluorescent material; an isotope; a material responsive to a light, an electromagnetic wave, or heat; a pharmacologically active material; or combinations thereof.

In the contrast agent for X-ray computed totmography, according to the present invention, the tantalum oxide may be TaO.

Further object of the present invention can be achieved by providing a method for preparing a surface-modified tantalum oxide nanoparticle/polymer nanocomposition, comprising: (i) adding an aqueous phase to an organic solvent which contains a surfactant, to prepare a water-in-oil microemulsion; (ii) introducing a tantalum precursor to said microemulsion; (iii) adding a surface-modifier having an organic silane group or phosphine group to a solution obtained at the step (ii); (iv) removing said organic solvent from a product obtained at the step (iii); (v) separating surface-modified tantalum oxide nanoparticles from a mixture obtained at the step (iv); and (vi) adding said surface-modified tantalum oxide nanoparticle to a solution containing a polymer, followed by heating the thus obtained mixture to remove said solvent, and a highly dielectric film prepared by a method comprising applying the surface-modified tantalum oxide nanoparticle/polymer nanocomposition on a substrate.

The polymer may be a polyurethane copolymer, a cellulose derivative, poly(methyl methacrylate) (PMMA), poly(methyl acrylate) (PMA), a polyacryl copolymer, poly(vinyl acetate) (PVAc), a poly(vinyl acetate) copolymer, poly(vinyl alcohol) (PVA), poly(furfuryl alcohol) (PFA), polystyrene, a polystyrene copolymer, poly(ethylene oxide) (PEO), poly(propylene oxide) (PPO), a poly(ethylene oxide) copolymer, polycarbonate (PC), poly(vinyl chloride) (PVC), polycaprolactone, poly(vinyl pyrrolidone) (PVP), poly(vinyl fluoride), poly(vinylidene fluoride), polyimide, poly(ethylene terephthalate) or combinations thereof.

The polymer may be added to a reaction mixture, as a solution in an appropriate solvent that can dissolve the polymer. For example, an organic solution containing the polymer may be added to the reaction mixture. The organic solvent may be alcohol, aromatic solvent (e.g., toluene, etc.), but not limited thereto.

Except the step (vi) of the method for preparing a surface-modified tantalum oxide nanoparticle/polymer nanocomposition, the steps (i) to (v) are the same as those of the method for preparing a surface-modified tantalum oxide nanoparticles of the present invention.

The aqueous phase may further comprise a hydrophilic solvent. The hydrophilic solvent may be $C_{1-8}$ alcohol, acetonitrile, $C_{1-8}$ ether or acetone. Preferably, the hydrophilic solvent may be ethanol.

The highly dielectric film of the present invention may be prepared by a liquid coating method that applies on a substrate a solution produced by dissolving the surface-modified tantalum oxide nanoparticle/polymer nanocomposition to an organic solvent such as toluene, but not limited thereto.

The liquid coating method may include conventional liquid coating methods, for example, a spin coating process, a dip coating process, a screen printing process, etc., that can form a film on a substrate.

Advantageous Effects

According to the method for preparing a surface-modified tantalum oxide nanoparticle, the surface-modified tantalum oxide nanoparticle may be prepared simply and easily and may be produced in a large scale, i.e., gram-scale or above. In addition, the surface-modified tantalum oxide nanoparticles may be prepared in a large scale at very low costs since the steps of preparing microemulsions to modifying the surface of the nanoparticle may be carried out continuously in a single reactor at a relatively low temperature and the solvent may be recycled The surface-modified tantalum nanoparticles prepared by the present invention is applicable to various applications such as highly dielectric film for OTFT, an X-ray contrast agent, etc.

As an X-ray contrast agent, the surface-modified tantalum nanoparticles prepared by the present invention have properties equivalent or superior to gold nanoparticles, for example, high X-ray absorption ability, excellent biocompatibility, prolonged circulation time, etc.

Since the highly dielectric film prepared by the present invention, which includes surface-modified tantalum oxide nanoparticles, may reduce the roughness of the film surface and enhance the performance of the OTFT, the highly dielectric film of the present invention is applicable to an ideal dielectrics in terms of simple manufacturing process, cost-effectiveness and performance.

BRIEF DESCRIPTION OF THE DRAWINGS

FIG. 22a shows in vivo CT volume-rendered (upper left) and maximum intensity projections (MIP) images (upper right and lower panels) of sentinel lymph node of the rat, obtained 2 hr after intradermal injection of 100 μL of PEG-RITC-TaO$_x$ solution (210 mg/mL) in both paws. The yellow circles and arrows indicate the locations of the lymph nodes. FIG. 22b illustrates white light photographs (upper panels) and fluorescence images (lower panels) of the rat injected intradermally with 100 μL of PEG-RITC-TaOx solution in both paws. Lateral views of the rat 2 h after injection show highly intense red emission from the lymph node and injected part (left and middle). Arrows and circles indicate the putative axillary sentinel lymph nodes and injection point, respectively. Sentinel lymph nodes of the two rats dissected by bimodal image-guided surgery (right).

Best Mode

Figure 1:
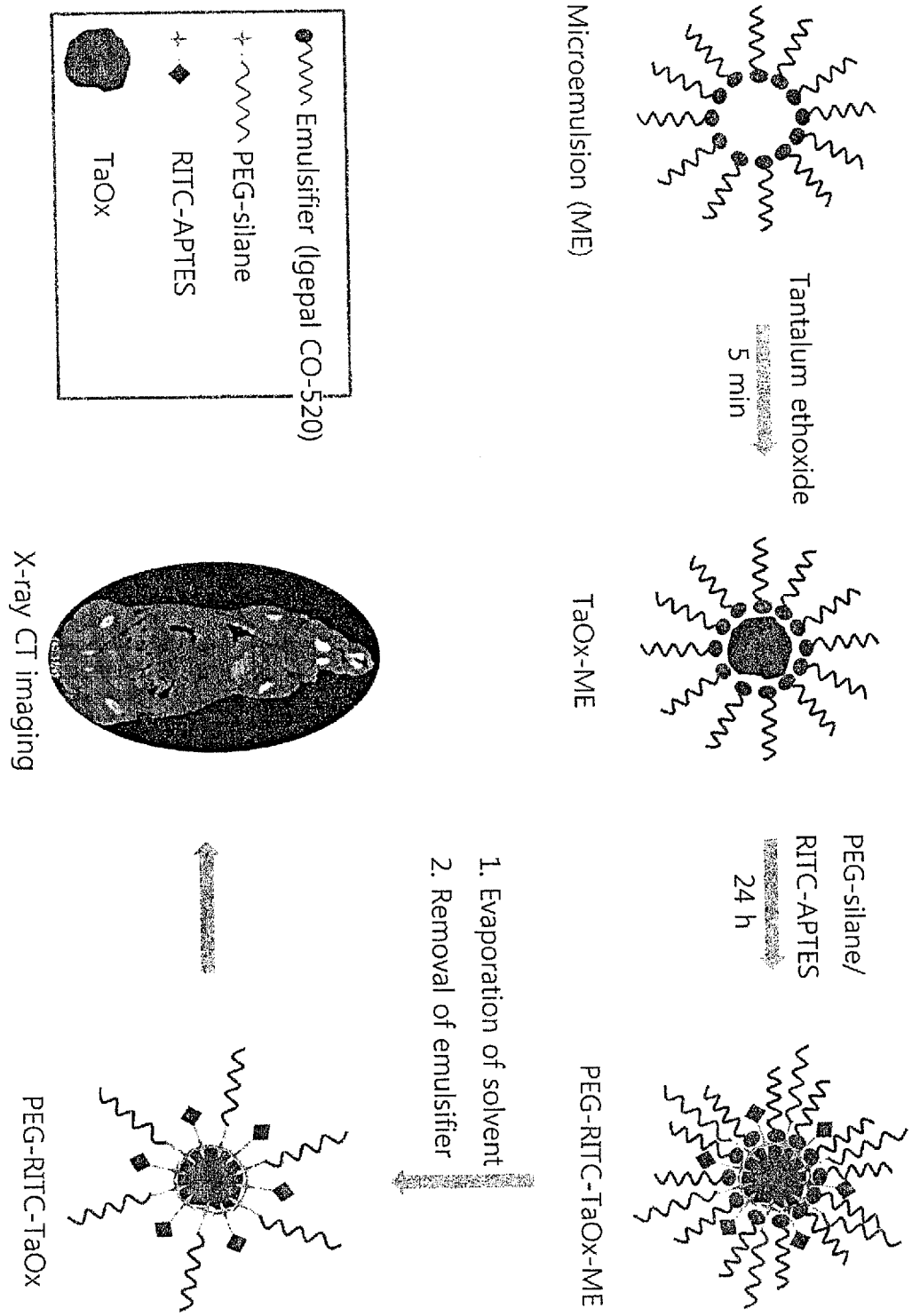
FIG. 1 is a flow diagram that shows one embodiment of the method for preparing a surface-modified tantalum oxide nanoparticle of the present invention.

Hereinafter, the present invention will be described in greater detail with reference to the following examples and drawings. The examples and drawings are given only for illustration of the present invention and not to be limiting the present invention.

EXAMPLE 1.

Synthesis of TaO$_x$ Nanoparticles in Microemulsion

Microemulsion (ME) was prepared by adding 0.25 mL of NaOH aqueous solution (75 mM) to oil phase composed of 2.3 g of Igepal CO-520 (Aldrich), ethanol (Samchun, 99.5%), and 20 mL of cyclohexane (Samchun, 99.5%). After 0.05 mL of tantalum (V) ethoxide (0.3 mmol, Strem, 99.8%) was added to the ME at room temperature, a resulting mixture containing tantalum oxide nanoparticles (designated as TaO$_x$-ME) was synthesized within 5 min. The amount of ethanol was varied (0, 0.25, 0.5, and 0.75 mL) to control the size of the TaO$_x$ nanoparticles.

EXAMPLE 2.

One-Pot Surface Modification of TaO$_x$ Nanoparticles

In order to collect the tantalum oxide nanoparticles for the ME without aggregation after decay of the micelle structure, appropriate amounts of TOP, APS, MPTMS, PEG-silane or TEOS were introduced in the last step of preparing the tantalum oxide nanoparticle.

Trioctylphosphine-stabilized Tantalum Oxide Nanoparticles

In order to synthesize trioctylphosphine (TOP)-stabilized tantalum oxide nanoparticles, the ME with 4 mL of TOP was evaporated at 60° C. Then, a solution of TOP-stabilized tantalum oxide nanoparticles and NP-5 was washed several times with a solvent/nonsolvent precipitation method using chloroform and methanol, followed by centrifugation at 2,000 rpm for 30 min. The thus obtained nanoparticles were well dispersed in an organic solvent such as chloroform or toluene.

Surface-modification of Tantalum Oxide Nanoparticles with Organosilane

Organosilane-modified tantalum oxide nanoparticles were prepared by reacting TaO$_x$-ME with 3-aminopropyltriethoxysilane (APS, 0.1 mL), methacryloxypropyltrimethoxysilane (MPTMS, 0.5 mL) and PEG-silane (0.05 mL), respectively, at room temperature for 24 hours. Then, the tantalum oxide nanoparticles of which surfaces were modified with the organosilane, were precipitated. After reaction, the thus obtained solution was evaporated at 60° C. in order to complete the surface-modifying reaction. As a result, the solution became transparent. Unreacted organosilane and NP-5 were dissolved into hexane or a mixture solution of ethanol/hexane (1:1, in the case of PEG-silane). Precipitated residual nanoparticles were centrifuged at 2,000 rpm and washed several times with solvent/nonsolvent (acetone/hexane). MPTMS-grafted tantalum oxide nanoparticles were well dissolved in an organic solvent such as ethanol or chloroform. APS-grafted, amino-functionalized tantalum oxide nanoparticles were dissolved in ethanol by ultrasonic treatment for 3 hours. Pegylated tantalum oxide nanoparticles were well dissolved in water by ultrasonic treatment for a few minutes.

One-pot Silica Coating of Tantalum Oxide Nanoparticles

TEOS (0.3 mL) was added to $TaO_x$-ME and the thus obtained solution was stirred at room temperature for more than 6 hours. Then, ammonia solution (30%) was added to the solution, followed by mixing for 3 hours. 3 mL of ethyl acetate was added to the solution and silica shell was grown slowly on the surface of the tantalum oxide nanoparticle for 24 hours.

EXAMPLE 3.

Preparation of Tantalum Oxide Nanoparticle/Polymer Nanocomposition and Highly Dielectric Film $TaO_x$/PMMA Nanocomposition and Film MTPMS-grafted TaOx nanoparticles which were prepared in Example 2 and dissolved in 10 mL of chloroform, were added to toluene solution containing 0.5 g of PMMA. The MPTMS-$TaO_x$/PMMA solution was heated at 60° C. for 24 hours with stirring until toluene/chloroform are completely evaporated. The thus obtained powders were dissolved in chloroform/toluene mixture (v/v=0.25~1) and one drop (5~10 μL) of the solution was located on the surface of deionized water contained in a petri dish with a diameter of 10 cm. After 30 minutes, transparent MPTMS-$TaO_x$/PMMA film was formed and, then, deposited on an ITO glass which was already located in the bottom of the petri dish, by removing the ionized water with a pipette.

TOP-stabilized TaOx nanoparticles which were prepared in Example 2 and dissolved in 10 mL of chloroform, were added to toluene solution containing 0.5 g of PMMA. According to the same method as that of formation of the MPTMS-$TaO_x$/PMMA film, a mixed solution was evaporated with a rotary evaporator and the thus obtained powders were dissolved in 30 mL of toluene. Transparent TOP-$TaO_x$/PMMA film was deposited on an ITO glass.

$TaO_x$/PMMA Nanocomposition $TaO_x$-ME was mixed with 15 mL of ethanol solution containing 0.16 g of poly(4-vinylpyridine) (P4VP) and the thus obtained mixture was heated at 90° C. for 1 hour, followed by evaporation at 60° C. for 15 minutes with a rotary evaporator. The resulting powders were washed several times with hexane to remove NP-5 and dissolved in ethanol.

EXAMPLE 4.

Pegylation and Rhodamine B Isocyanate (RITC) Functionalization of $TaO_x$ Nanoparticles for Bimodal Imaging Applications In order to prepare rhodamine β isocyanate (RITC)-functionalized silane, 110 μL of aminopropyltriethoxysilane (APTES, Aldrich) was reacted with 50 mg of RITC in 3.75 mL of ethanol at room temperature for 24 h. The resulting solution along with 12.5 mL of 2-methoxy(polyethylenoxy)propyltrimethoxysilane (PEG-silane, Gelest, 596~725 Da) was added to 1 L of the $TaO_x$-ME prepared in Example 1. The mixture was then stirred at room temperature for 24 h, becoming a red turbid solution. The resulting solution was evaporated at 60° C. until the solution became transparent, after which the functionalized $TaO_x$ nanoparticles were precipitated by adding a mixed solution of 1:1 (v/v) ether/n-hexane. The precipitates were purified with ether and dispersed in ethanol. To this solution, 100 mg of methoxypoly(ethylene glycol) succinimidylglutarate (mPEG-SG, MW 2000, Sunbio) was added. The mixture was stirred overnight at 30° C. to conjugate PEG onto residual amine groups on the surface of the functionalized $TaO_x$ nanoparticles. After washing several times with deionized water, the final product, designated as PEG-RITC-$TaO_x$, was dispersed in phosphate buffered saline (PBS) buffer.

X-Ray CT and Fluorescence Imaging with PEG-RITC-$TaO_x$ Phantom Test:

Various concentrations of PEG-RITC-$TaO_x$ (0.22, 0.45, 0.9, 1.8, 3.6, 7.2, 14.5, and 29 mg of Ta/mL) dispersed in deionized water were prepared in 1.5 mL microtubes. CT images were acquired using a dual-source CT system (Somatom Definition, Simens). Imaging parameters were as follows: thickness, 1 mm; pitch, 1; 120 kVp, 90 mA; field of view, 84×84; gantry rotation time, 0.5 s; table speed, 6 mm/s.

Cell Culture:

RAW264.7 (murine macrophage cell line) was grown in monolayers in Dulbecco's Modified Eagle's Medium (DMEM, WeIGENE) supplemented with 10% (v/v) fetal bovine serum (FBS, Gibco) and penicillin/streptomycin (100 U/mL and 100 μg/mL, respectively, Gibco) in a humidified 5% $CO_2$ atmosphere at 37° C.

Cellular Uptake:

To observe cellular uptake of the $TaO_x$ nanoparticles, $1 \times 10^4$ RAW 264.7 cells per well were cultured in an 8-well chamber slide (NalgenNunc, Naperville, Ill.) and incubated with PEG-RITC-TaOx at various concentrations (0, 0.6, 1.2, and 2.4 mg of Ta/mL). After 24 hr, the cells were washed with PBS, fixed with 4% paraformaldehyde, and stained with 4',6-diamidino-2-phenylindole (DAPI, 1 μg/mL in PBS, Roche). Fluorescence images were acquired by confocal laser scanning microscopy (CLSM) (LSM 510, Carl Zeiss, Germany).

Cell Viability Assay:

The viability and proliferation of cells in the presence of TaOx nanoparticles were evaluated by 3-[4,5-dimethylthiazol-2-yl]-2,5-diphenyltetrazolium bromide (MTT, Sigma) assay. The assay was performed in triplicate in the following manner. RAW264.7 cells were seeded into 96-well plates at a density of $1 \times 10^4$ cells per well in 200 μL of media and grown overnight. The cells were then incubated with various concentrations of PEG-RITC-$TaO_x$ (0, 0.075, 0.15, 0.3, 0.6, 1.2, and 2.4 mg of Ta/mL) for 24 h. Following incubation, cells were incubated in media containing 0.1 mg/mL of MTT for 1 h. Thereafter, MTT solution was removed, and precipitated violet crystals were dissolved in 200 μL of DMSO. The absorbance was measured at 560 nm using a VersaMax™ microplate reader (Molecular Devices).

In vitro CT Imaging:

RAW264.7 cells were seeded onto culture dishes at a density of $1 \times 10^6$ cells per plate in 10 mL of media and grown overnight. Subsequently, various concentrations of PEG-RITC-TaOx (0, 0.63, 1.3, and 2.5 mg of Ta/mL) dispersion were added. After 24 h, the cells were washed twice with PBS to remove free nanoparticles and detached by the addition of 1 ml of trypsin/EDTA (Gibco). After centrifugation at 1500 rpm for 5 min, cells were dispersed in 1 mL of culture media and transferred to a 1.5 mL microtube. Cell pellets were prepared by centrifugation at 2000 rpm for 5 min.

CT images were acquired using a dual-source CT system (Somatom Definition, Simens). Imaging parameters were as follows: thickness, 1 mm; pitch, 1; 120 kVp, 90 mA; field of view, 84×84; gantry rotation time, 0.5 s; table speed, 6 mm/s.

In vivo CT Imaging:

CT images were acquired prior to injection of PEG-RITC-TaO$_x$ as well as at appropriate time points after administration. Rats were anesthetized by intraperitoneal injection of a mixture of Zoletil (1.92 mg/kg; Virbac, France), Rompun (0.48 mg/kg; Bayer Korea, Korea), and saline. Then, 1 mL of PEG-RITC-TaO$_x$ dispersion (840 mg/kg) was injected through the tail vein of the rat.

For lymph node imaging, 100 µL of the PEG-RITC-TaO$_x$ solution was injected intradermally into the paws of rats, which were repeatedly imaged up to 2 h after injection.

CT images were acquired using a Brilliance 64-slice CT Scanner (Philips Medical System). Imaging parameters were as follows: thickness, 0.1 mm; pitch, 0.648; 120 kVp, 192 mA; field of view, 108×108; matrix, 1024×1024 pixels; gantry rotation time, 0.75 s; table speed, 16.7 mm/s. Thin-section axial images were reformed to coronal images through a computational technique referred to as multiplanar-reconstruction (MPR). The three-dimensional (3-D) reconstructed images were obtained using OsiriX (Version 3.8.1; 32 bit; OsiriX foundation, Geneva).

In vitro and in vivo Fluorescence Imaging:

In vitro and in vivo fluorescence images were acquired using a fluorescence imaging system at an excitation wavelength of 550 nm (Kodak IS4000MM pro, US).

Results

Figure 2:
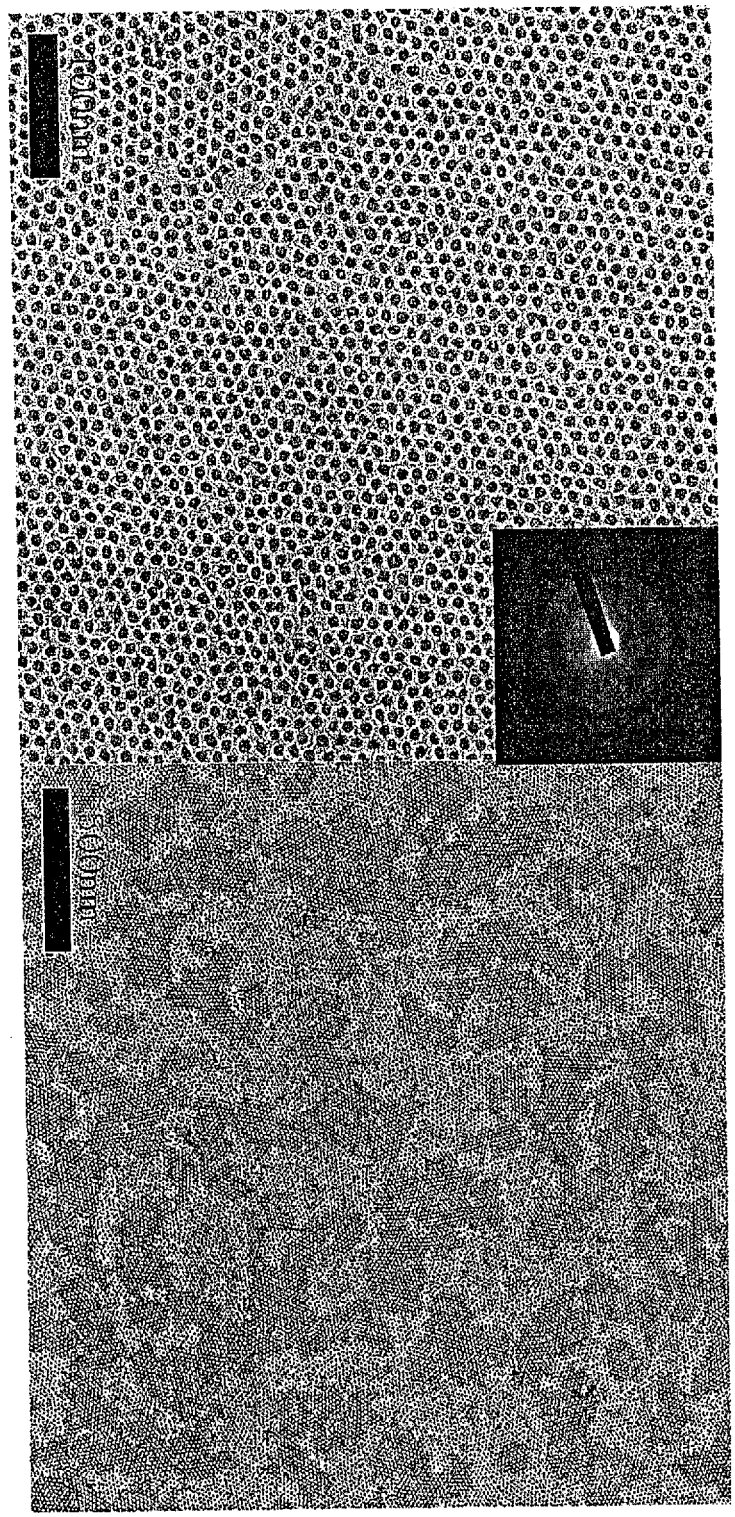
FIG. 2 is TEM images of the tantalum oxide nanoparticles prepared by the method of the present invention.

FIG. 1 illustrates the overall process for synthesis of a surface-modified tantalum oxide nanoparticle, as described in Example 1, and an X-ray CT image obtained with the nanoparticle. In Example 1, NaOH aqueous solution as a base catalyst for the sol-gel reaction of tantalum (V) ethoxide, instead of typical ammonia catalyst used in silica sol-gel reactions was used since the reaction rate of tantalum (V) ethoxide is much faster than that of TEOS and ammonia catalyst which would lead to uncontrolled agglomeration of nanoparticles. After emulsification of a mixture composed of cyclohexane, ethanol, NaOH and Igepal CO-520 surfactant, tantalum (V) ethoxide was added to the emulsion. Controlled sol-gel reaction in the reverse micelles at room temperature led to the formation of uniform nanoparticles within 5 min. Transmission electron microscopy (TEM) image of the as-prepared TaO$_x$ nanoparticles in micelles (TaO$_x$-ME) showed that the size distribution of the nanoparticles was very narrow ($\sigma_r \leq 5\%$) (FIG. 2).

Figure 3:
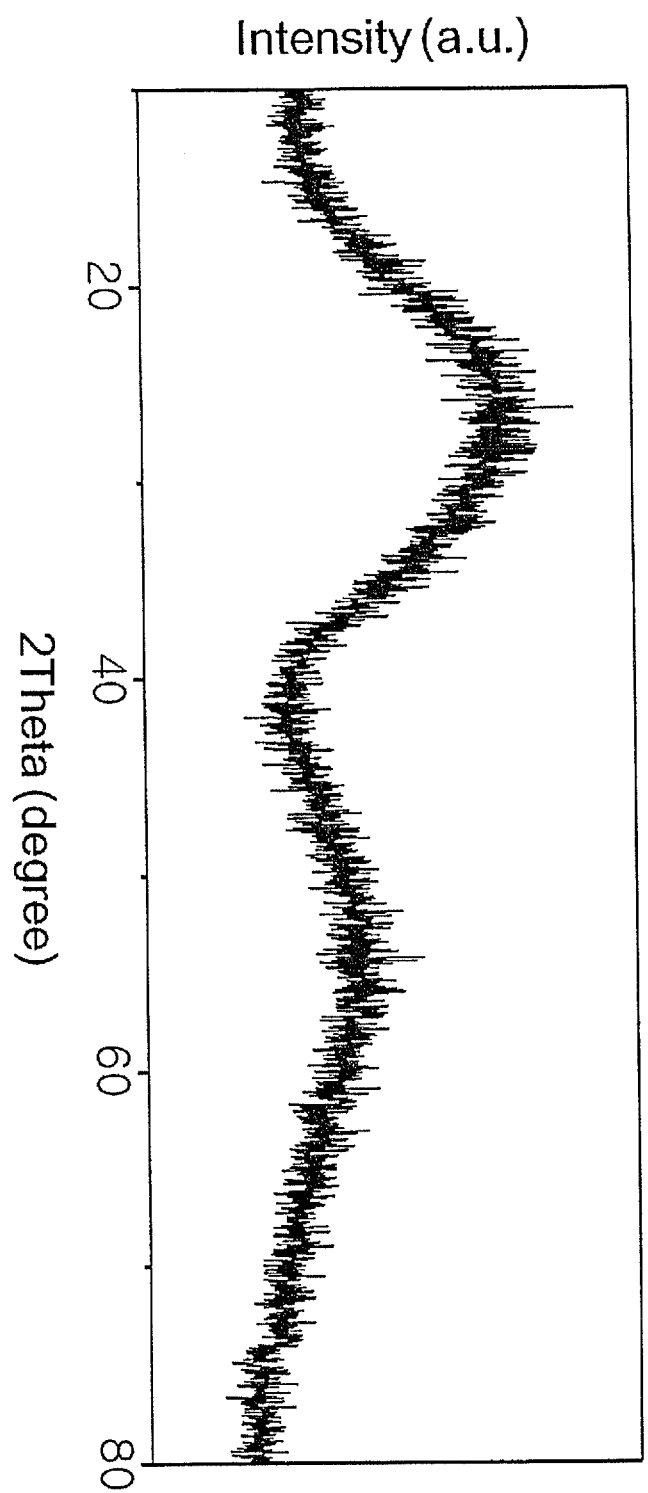
FIG. 3 is an XRD pattern of amorphous tantalum oxide nanoparticles prepared by the method of the present invention.
Figure 4:
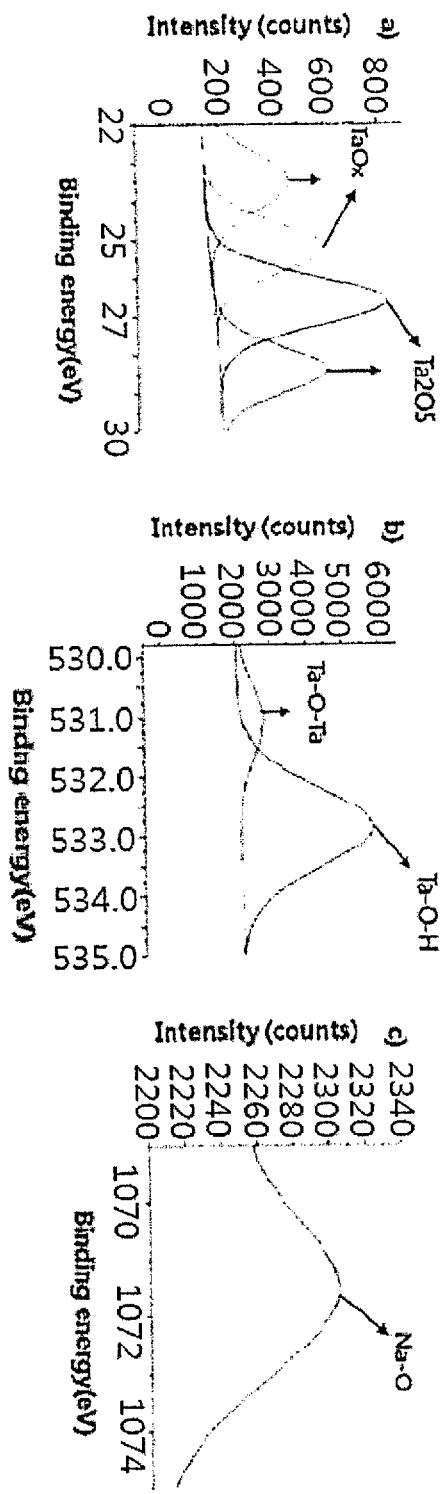
FIG. 4 shows the results of XPS analysis of the tantalum oxide nanoparticles prepared by the method of the present invention ((a) Ta 4f, (b) O 1s and (c) Na 1s peaks of the tantalum oxide nanoparticles).
Figure 5:
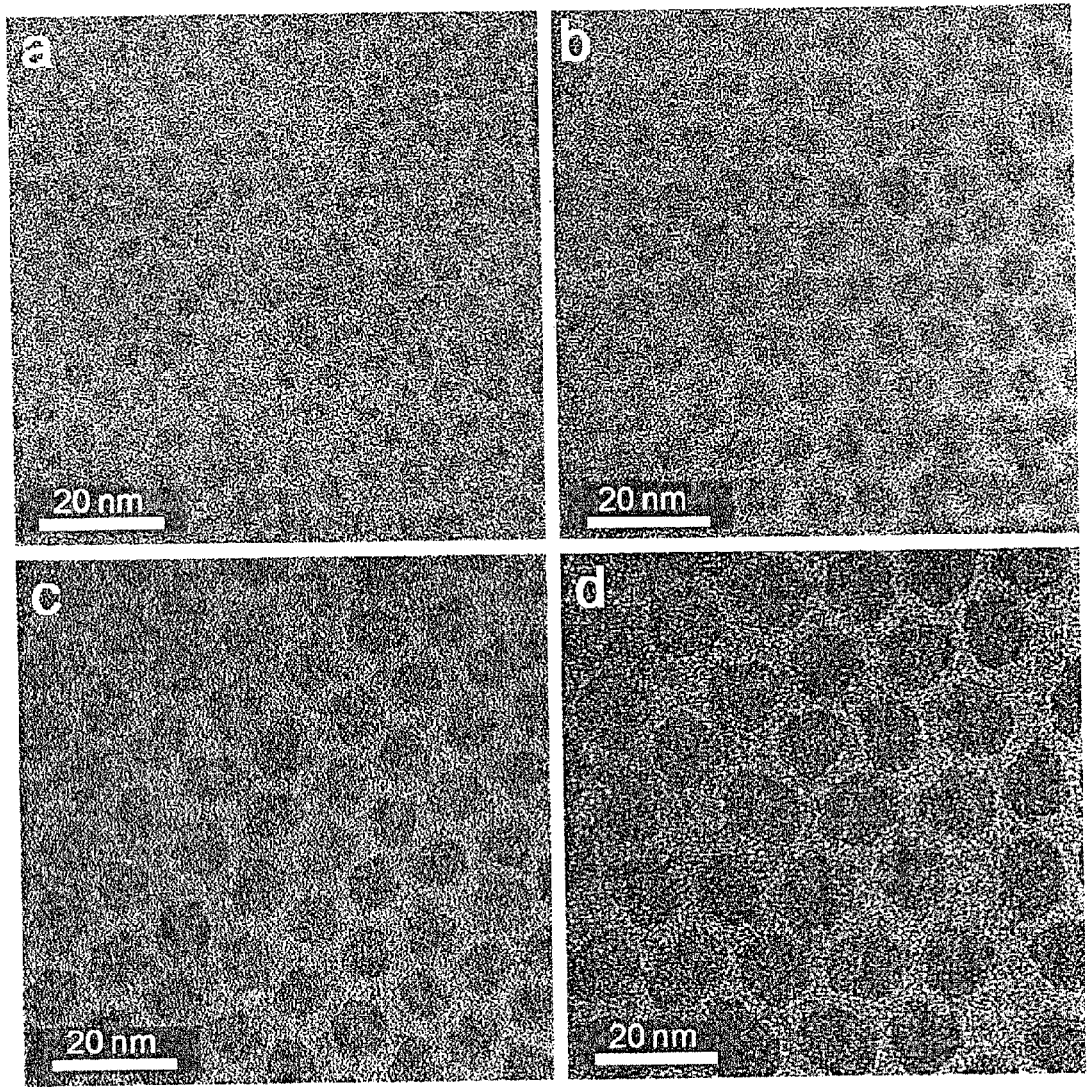
FIG. 5 shows TEM images of the tantalum oxide nanoparticles prepared by the method of present invention, of which sizes are changed by the amount of ethanol (a: 6 nm; b: 9 nm; c: 13 nm; d: 15 nm).

X-ray diffraction (XRD) (FIG. 3), electron diffraction (ED) (the inset of FIG. 2), and X-ray photoelectron spectroscopy (XPS) data (FIG. 4) revealed that the nanoparticles were amorphous and composed of tantalum sub-oxides (TaO$_x$, x~1) such as Ta$_2$O$_5$, TaO, etc. The size of the nanoparticles could be controlled in the range of 5 nm to 15 nm by varying the amount of ethanol (FIG. 5). The increased amount of ethanol seems to have resulted in decrease of hydrolysis rate of tantalum ethoxide, which eventually led to production of large nanoparticles.

Figure 6:
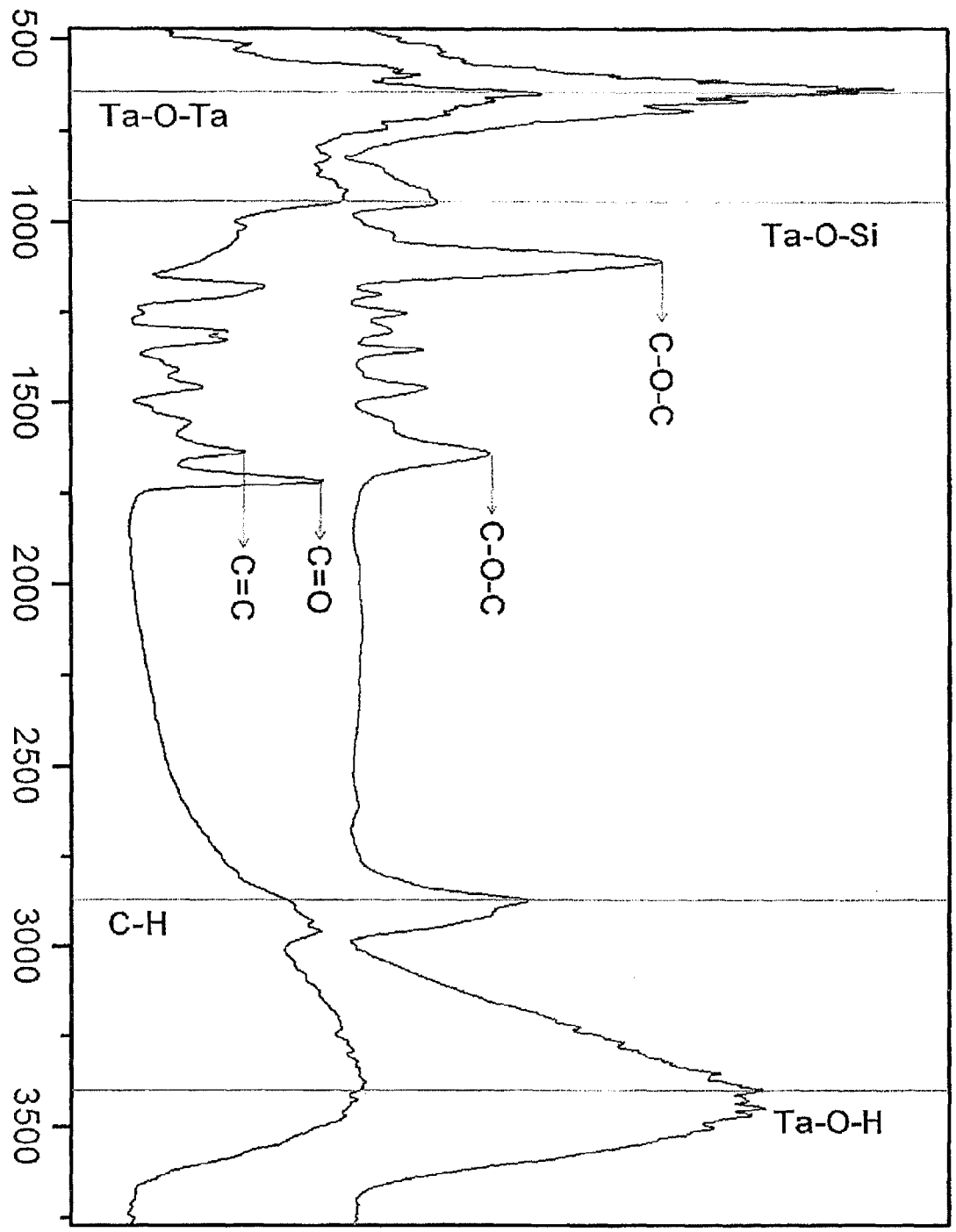
FIG. 6 shows FTIR spectra of the tantalum oxide nanoparticles of which surfaces have been modified by MPTMS and PEG-silane, according to the present invention.
Figure 7:
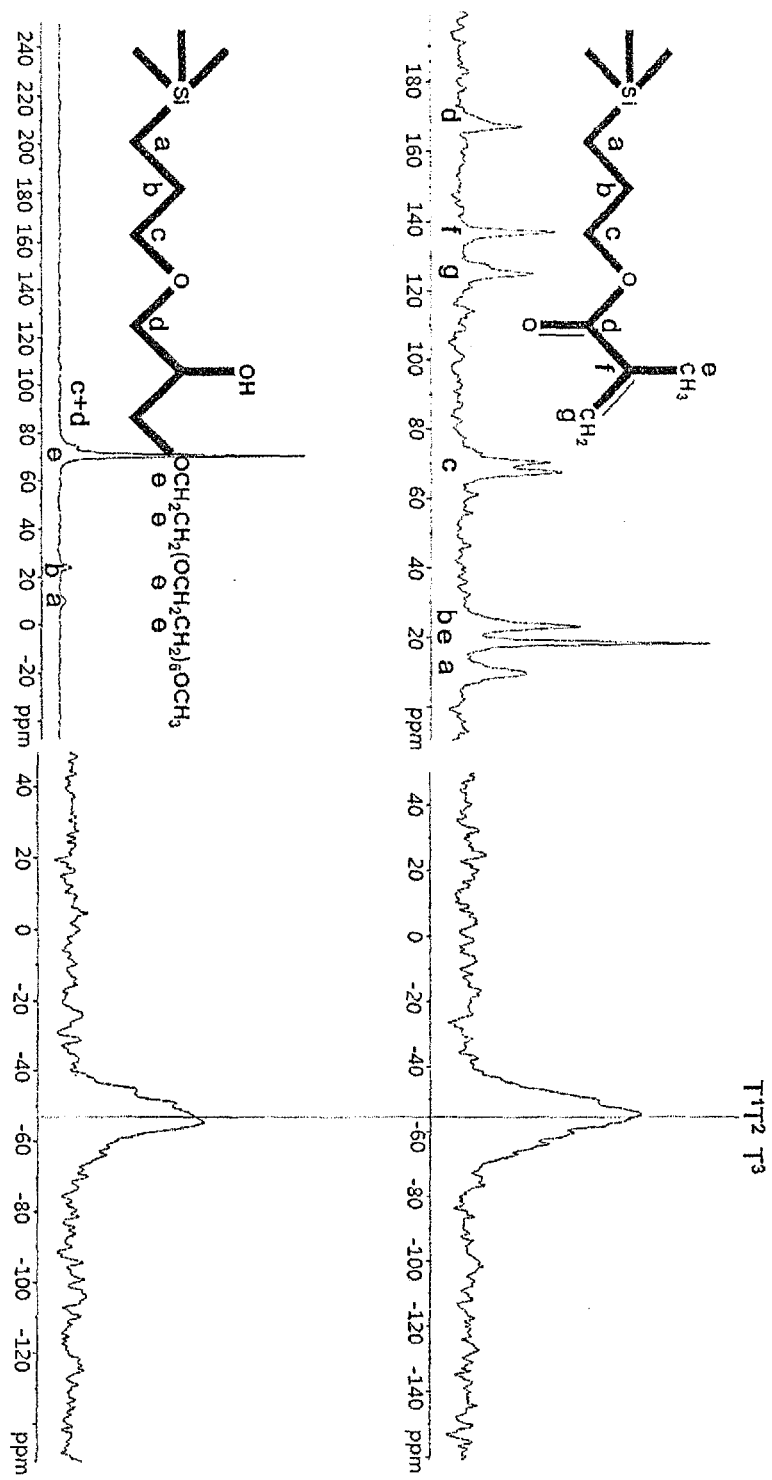
FIG. 7 shows $^{13}$C CP MAS NMR spectra of the tantalum oxide nanoparticles of which surfaces have been modified by (a) MPTMS and (b) PEG-silane, according to the present invention.
Figure 8:
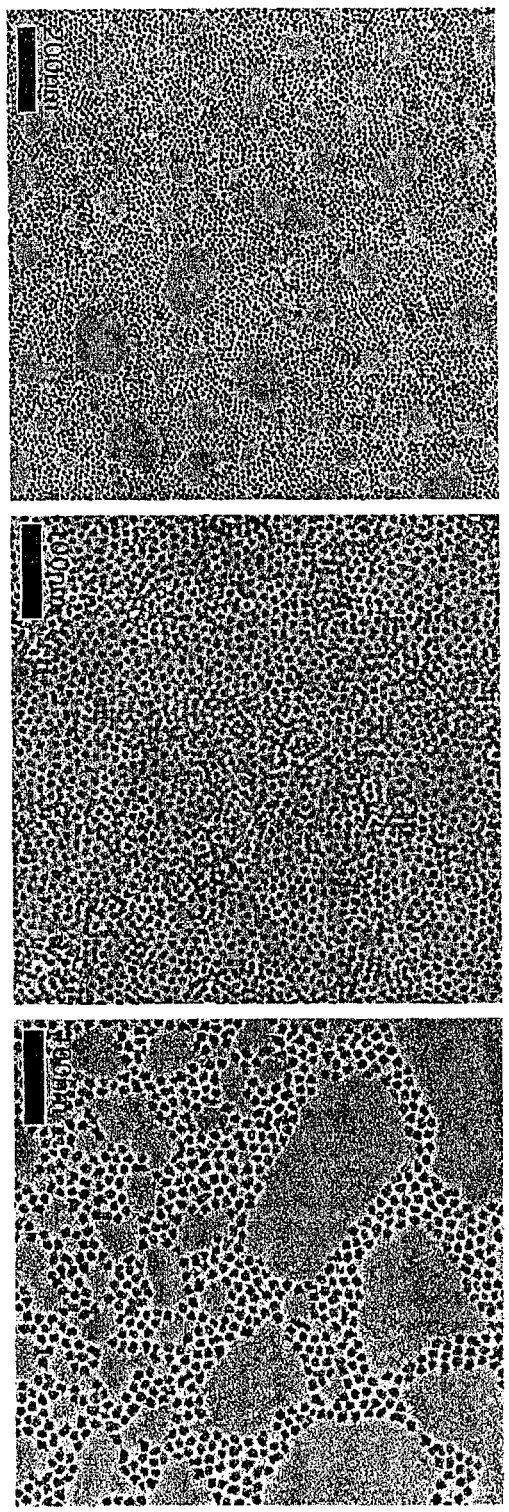
FIG. 8 shows TEM images of the tantalum oxide nanoparticles which are functionalized by (a) MPTMS, (b) TOP and (c) APS, according to the present invention.

When other solvents such as toluene, hexane or acetone was added to the microemulsion, tantalum oxide nanoparticles were rapidly aggregated by reaction between hydroxyl groups on the surface of the tantalum oxide nanoparticles, as well as destruction of the micelle structures. These demonstrate that covalent bonds between the tantalum oxide nanoparticles and the emulsifiers did not form. Therefore, surface coordination agents should be introduced via a one-pot (single reactor) reaction in order to obtain non-aggregated nanoparticles. Particularly, silane and TOP were strongly conjugated below the boiling point of the solvents (cyclohexane/ethanol/water) before aggregation of the tantalum oxide nanoparticles. Since the surface of the tantalum oxide nanoparticle is more acidic than that of silica, the silane easily bonded to the OH group of the tantalum oxide nanoparticle and TOP, as a ligand according to weak acid-base reaction, may form a coordination bond with Ta atom. Moreover, since the solvent is separated at 60° C. concurrently with formation of the coordination bond, the solvent may be recycled. This procedure make it possible to solve the problem that large amount of solvent is used in an microemulsion method and to scale-up the synthetic process. After washing the emulsifier several times, stabilized tantalum oxide nanoparticles were analyzed by FTIR, NMR and TEM in order to find out the bonding of the ligand (FIGS. 6, 7 and 8). The results of FTIR show the existence of the functional groups on the silane. The NMR peaks between the 50~60 (T$^2$) region demonstrate that only coordinately bonded ligands exist without the nanoparticles and three-dimensionally growing silane (T$^1$ or T$^3$). As shown in the TEM images, the nanoparticles are well dispersible and silica does not exist.

Figure 9:
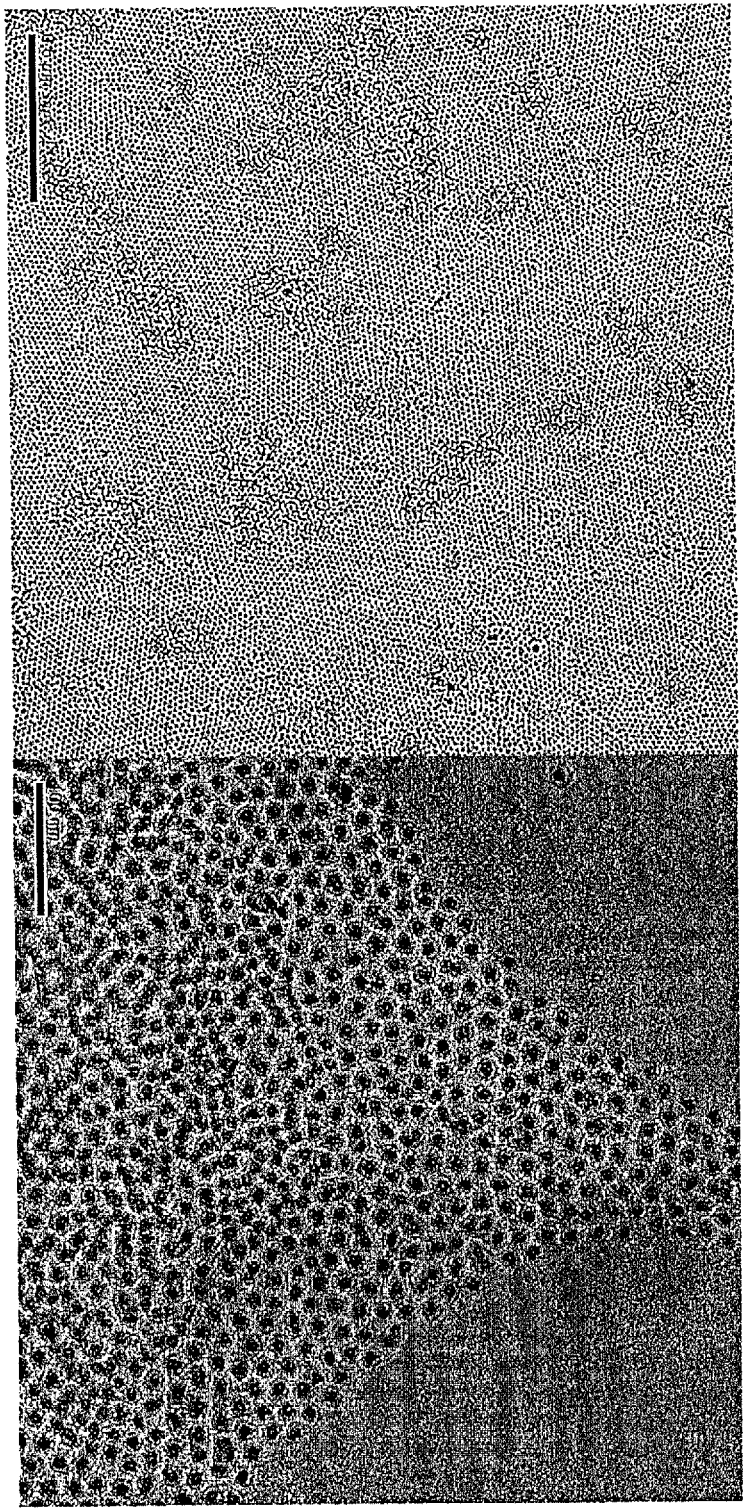
FIG. 9 shows TEM images of the silica-coated tantalum oxide nanoparticles prepared by the method of the present invention.

In addition, as described in Example 2, silica shell on the tantalum oxide nanoparticle was grown by changing the aqueous phase environment. Swelling of micelles is needed for growth of the shell. However, the micelle swelling induces aggregation of the tantalum oxide nanoparticles due to high reactiveness of the hydroxyl on the surface of the nanoparticle. Therefore, silanol groups which are less reactive, were formed on the surface of the nanoparticle by addition of TEOS before swelling of the nanoparticles. Ammonia solution was added as a swelling agent. When the pH of the aqueous phase was lowered by addition of ethyl acetate, the sol-gel reaction of TEOS was induced. As a result, uniform-sized silica shells were formed (FIG. 9).

The application of the tantalum oxide nanoparticle/polymer nanocomposition to a dielectric film for OTFT was investigated. As described in Example 3, the tantalum oxide nanoparticles incorporated into MPTMS and TOP-stabilized tantalum oxide nanoparticles were mixed with PMMA known as a dielectric substance. MPTMS-treated tantalum oxide nanoparticles were dissolved in ethanol to obtain long-term stability. To this solution, PMMA in toluene was mixed in a fixed ratio between the tantalum oxide nanoparticle and the PMMA. The thus obtained solution was evaporated by a rotary evaporator and dissolved in toluene to produce TaO$_x$/PMMA nanocomposition solution without aggregation. TOP-stabilized tantalum oxide nanoparticles were treated as the same method as that in the MPTMS-treated tantalum oxide nanoparticles. As reported by Brinker group, film was prepared at the interface between air and water. One drop of the MPTMS-TaO$_x$ solution was cast on the surface of deionized water in a petri dish of which at the bottom an ITO glass was located. After about 10 min, formation of thin film was induced by solidification of the PMMA and assembly of the nanoparticles. Finally, the ionized water was removed from the petri dish by using a pipette such that the film became located on the ITO glass, followed by soft-baking for 10 min. The thus prepared film was completely transparent and colorless. TEM images from the film obtained by deposition of TaO$_x$/PMMA nanocomposition on a grid instead of an ITO glass demonstrate that the pseudo-assembly of the nanoparticles in the PMMA film does not have any defects such as holes. The whole area of the TEM grid and even the area where the nanoparticles were not present were covered with PMMA. A part of the film, damaged by the beam of the TEM, was peeled off.

Figure 10:
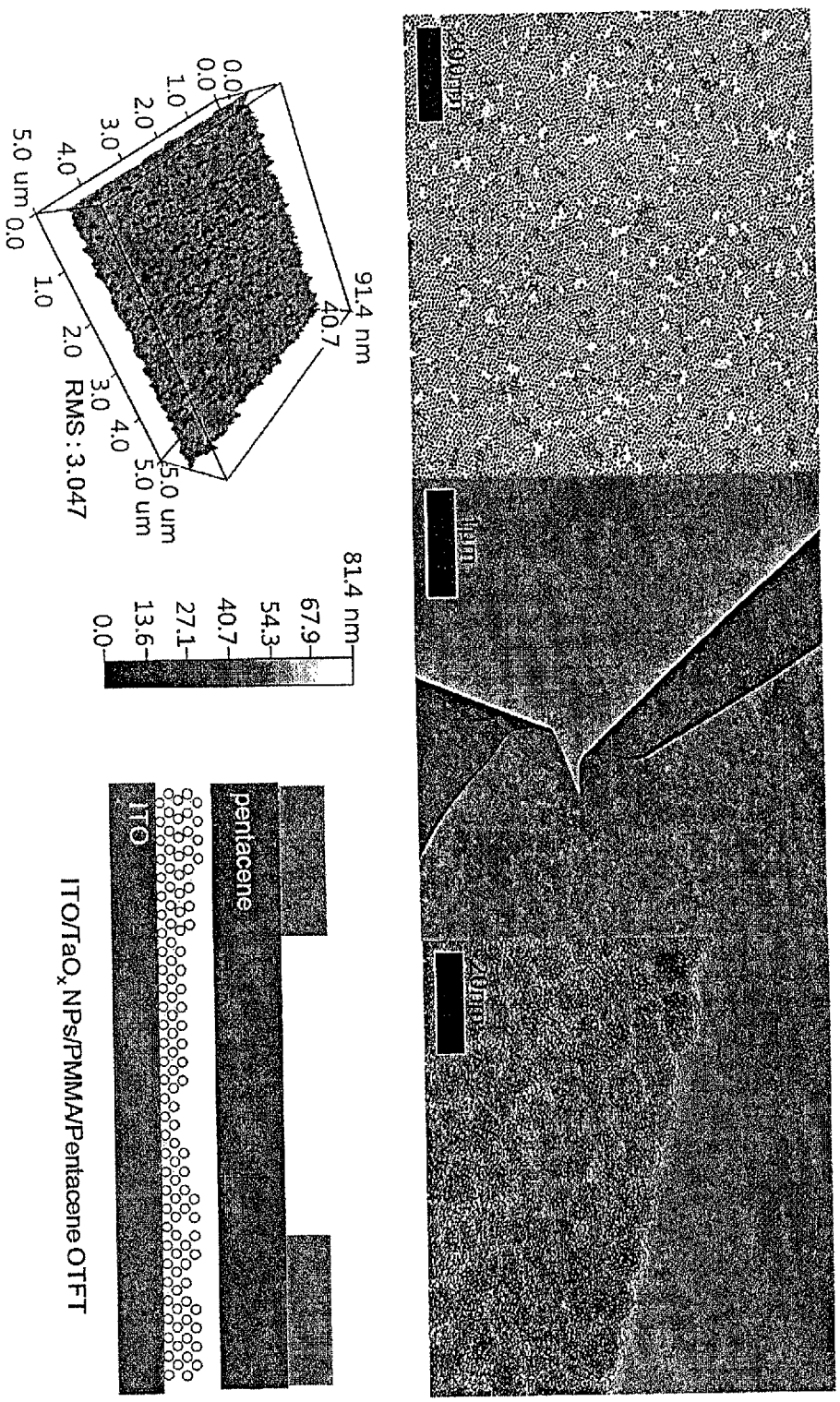
FIG. 10 shows (a, b and c) TEM images and (d) AFM image of the MPTMS-TaO$_x$/PMMA film prepared by the method of the present invention, and (e) the sectional view of the OTFT made of the MPTMS-TaO$_x$/PMMA film.
Figure 11:
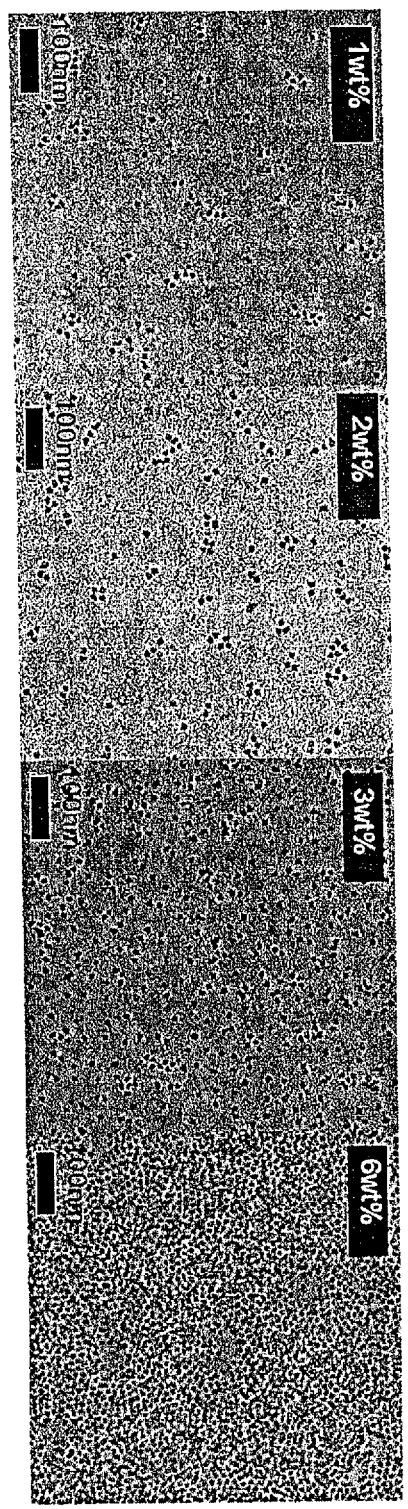
FIG. 11 shows TEM images of the MPTMS-TaO$_x$/PMMA films prepared with various concentrations of the TaO$_x$ nanoparticles ((a) 1 wt %, (b) 2 wt %, (c) 3 wt % and (d) 6 wt %), according to the present invention.

As shown in FIG. 10, the PMMA film with a thickness of 1~2 nm covered the assembled tantalum oxide nanoparticles. In addition, there were no tantalum oxide nanoparticles below the carbon film of the TEM grid even after the film was peeled and completely rolled-up. These results demonstrate that the whole area of the TEM grid was covered with PMMA. As the ratio of the solvent increased, the distance between the nanoparticles in the film increased. This is because the viscosity of the polymer at the interface between water and air was reduced (FIG. 11). The thickness profile and RMS data of the as-prepared film on the ITO glass, obtained by AFM analysis, proves that assembled nanoparticles and one or two layers of PMMA were formed over wide area. Consequently, the as-prepared polymer film has a potential to be used as a high-performance dielectric substance for the OTFT shown in FIG. 10e.

In Example 4, surface modification of the $TaO_x$ nanoparticles was directly performed using various silane agents without purification after the synthesis of the $TaO_x$-ME. Since the surface of unmodified $TaO_x$ nanoparticles is acidic and reactive toward condensation reactions, $TaO_x$ nanoparticles would be irreversibly aggregated without additional stabilization. Among the various silane moieties, PEG-silane and dye-conjugated silane were chosen since they are representative biocompatible polymer and fluorescent probe, respectively. Simple silica sol-gel reaction between the hydroxyl groups of the $TaO_x$-ME and silane reagents led to the formation of functionalized-silica-coated $TaO_x$ nanoparticles, which can be applied to multifunctional imaging platforms with multiple modality and/or targeting/therapeutic functions.

Figure 12:
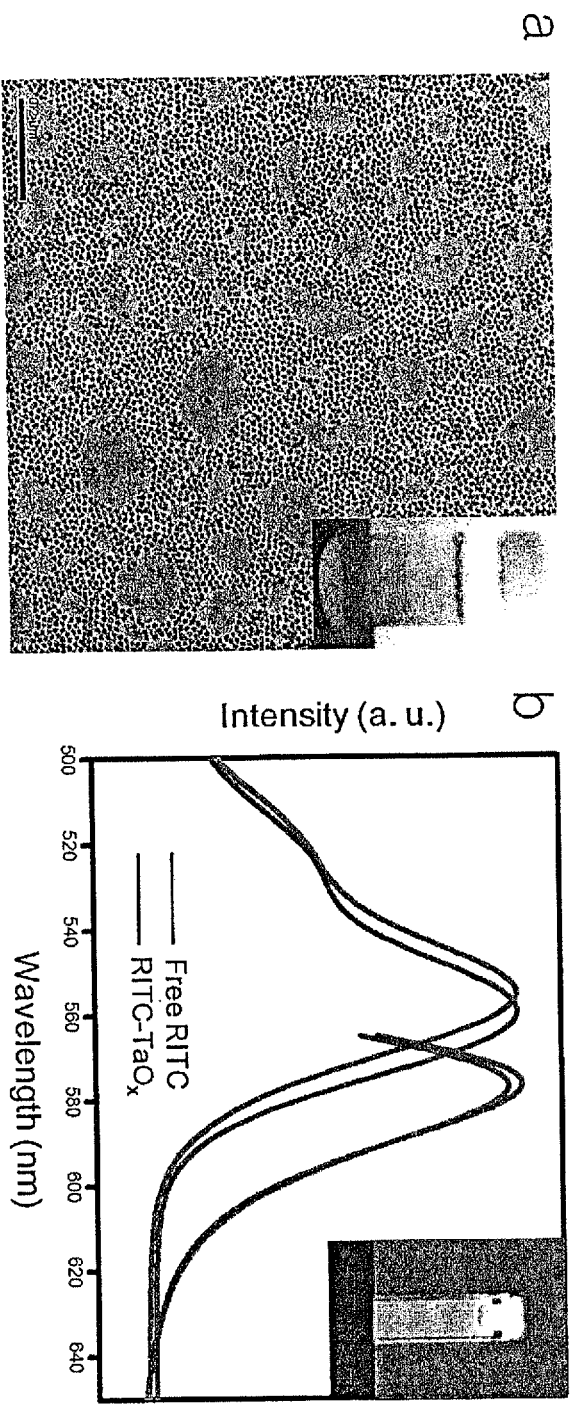
FIG. 12a shows a TEM image of the PEG-RITC-TaO$_x$ nanoparticles dispersed in water, prepared by the present invention, (inset: photograph of the aqueous dispersion of nanoparticles).
FIG. 12b shows absorbance and fluorescence spectra of the PEG-RITC-TaO$_x$ nanoparticle and free RITC in PBS solution, where optical densities were equalized to match the number of RITC molecules in both samples ($\lambda_{ex}$=520 nm, inset: photographic image of the fluorescent nanoparticles in PBS solution excited with UV light).
Figure 13:
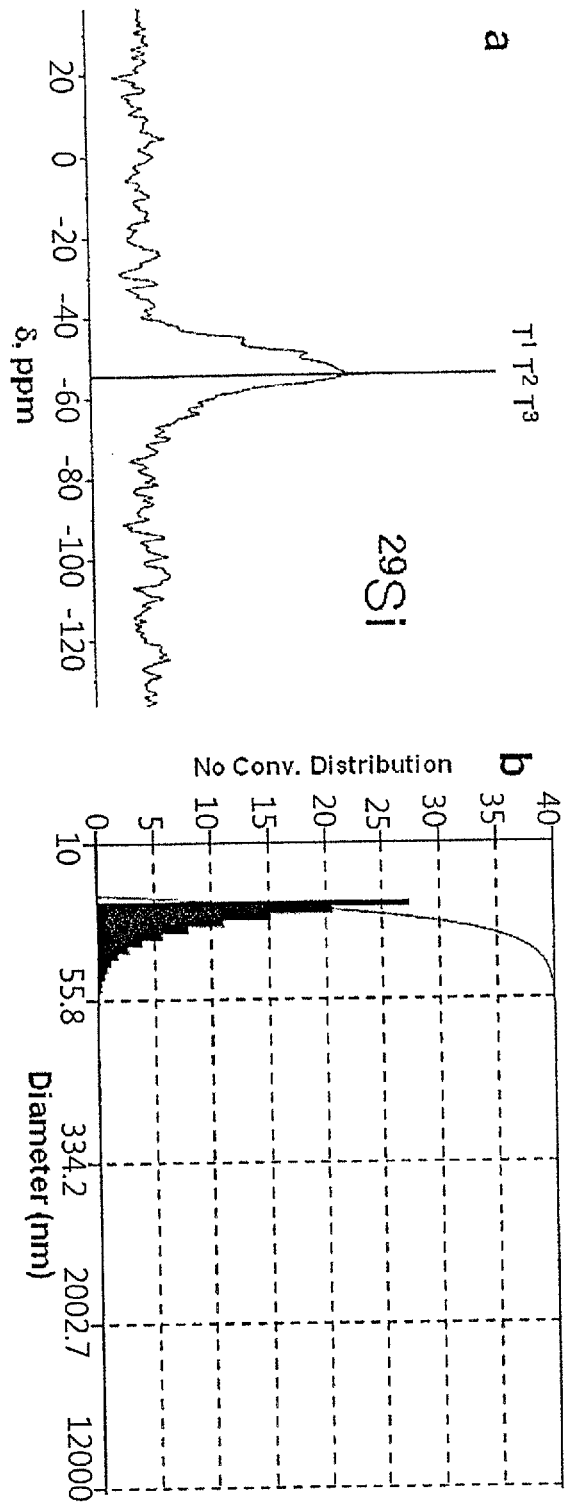
FIG. 13a illustrates $^{29}$Si CP MAS NMR spectra of PEG-silane immobilized TaO$_x$ nanoparticles showing characteristics of T$^2$ bonding peak and FIG. 13b shows size distribution of PEG-RITC-TaO$_x$ in PBS solution. Dynamic light scattering (DLS) measurement showed that average hydrodynamic diameter of the nanoparticles was 19 nm.

Long-circulating nanoparticles are required for effective X-ray CT imaging, such as angiography and tissue specific imaging. To avoid rapid clearance from the blood stream by reticuloendothelial system (RES) uptake, PEG-silane was immobilized on the $TaO_x$ nanoparticles as an anti-fouling agent. For fluorescence imaging, rhodamine B isocyanate (RITC)-conjugated aminopropyltriethoxysilane (APTES) was attached to the $TaO_x$ nanoparticles. RITC-conjugated-APTES and PEG-silane were simultaneously immobilized on the $TaO_x$-ME to produce tantalum oxide nanoparticles conjugated both with PEG and RITC, designated as PEG-RITC-$TaO_x$. TEM image of PEG-RITC-$TaO_x$ (FIG. 12a) showed that the nanoparticles were well dispersed in water, whereas no agglomerated nanoparticles were observed. $^{29}Si$ NMR spectroscopy revealed a single band corresponding to $T^2$ bonding sites centered at $\delta \sim -55$ ppm, demonstrating that PEG-silane formed on the surface of the nanoparticles while no separate silica particle formed (FIG. 13a). As shown in the inset of FIG. 12b, PEG-RITC-$TaO_x$ was transparent, which is advantageous for fluorescence imaging. RITC-conjugated $TaO_x$ exhibited comparable photoluminescence to free RITC, indicating that the conjugated dyes were stable and that their fluorescence was preserved even after the conjugation reaction. The hydrodynamic diameter (HD) of the particles as measured by dynamic light scattering (DLS) was approximately 19 nm, demonstrating that no aggregation occurred (FIG. 13b), which matched very well with the TEM data.

Figure 14:
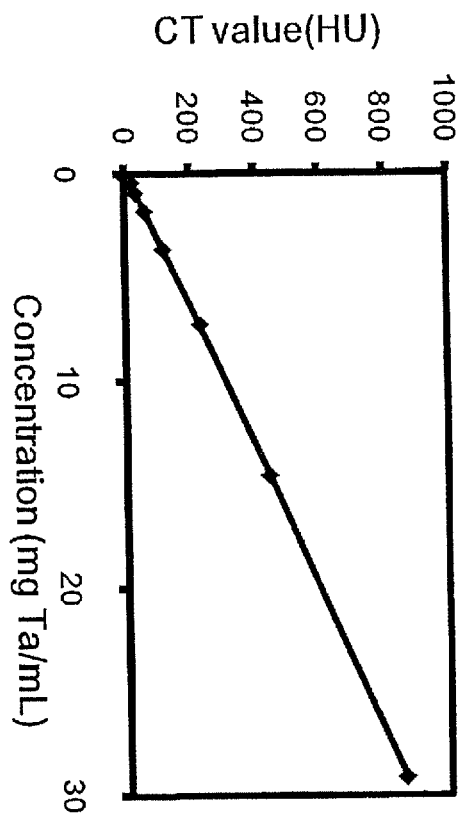
FIG. 14 shows HU measurements (left) and phantom CT image (right) of PEG-RITC-TaO$_x$ in water, according to in vitro characterization of PEG-RITC-TaO$_x$.
Figure 14:
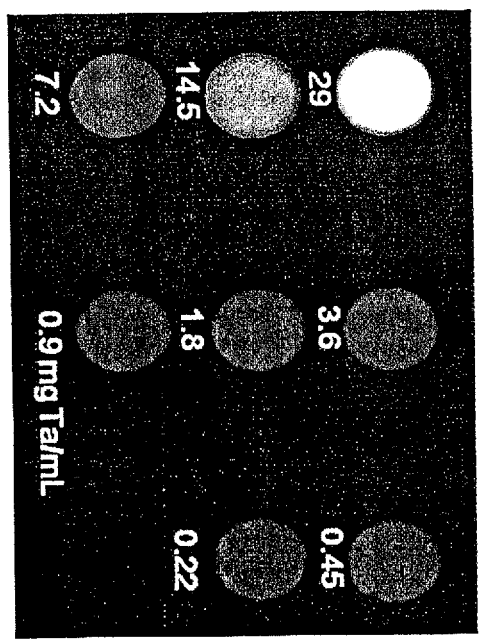
Figure 15:
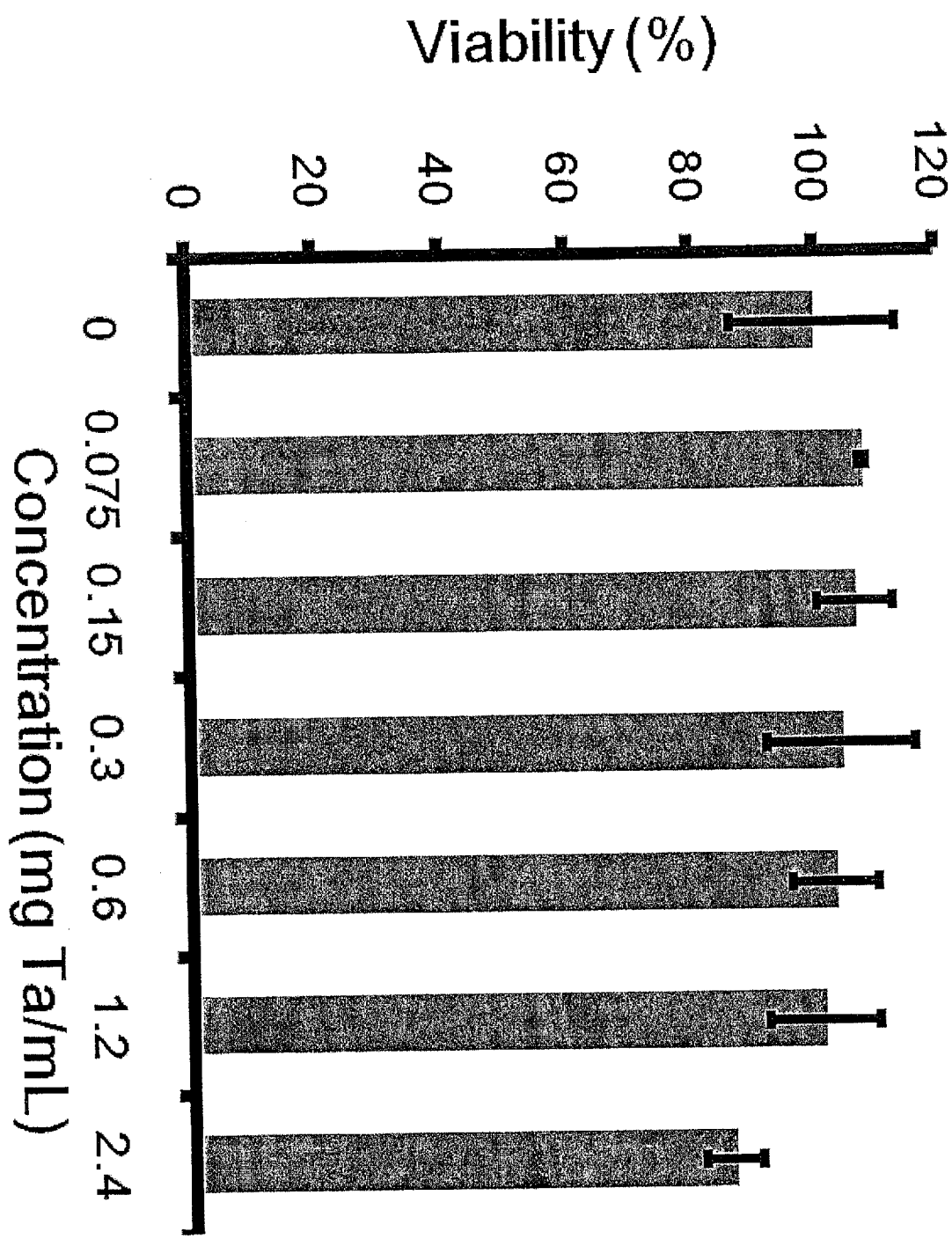
FIG. 15 shows cytotoxicity of the PEG-RITC-TaO$_x$ nanoparticles determined by MTT assay, where RAW264.7 cells (murine macrophages) were cultured with the nanoparticles of various concentrations, according to in vitro characterization of PEG-RITC-TaO$_x$.
Figure 16:
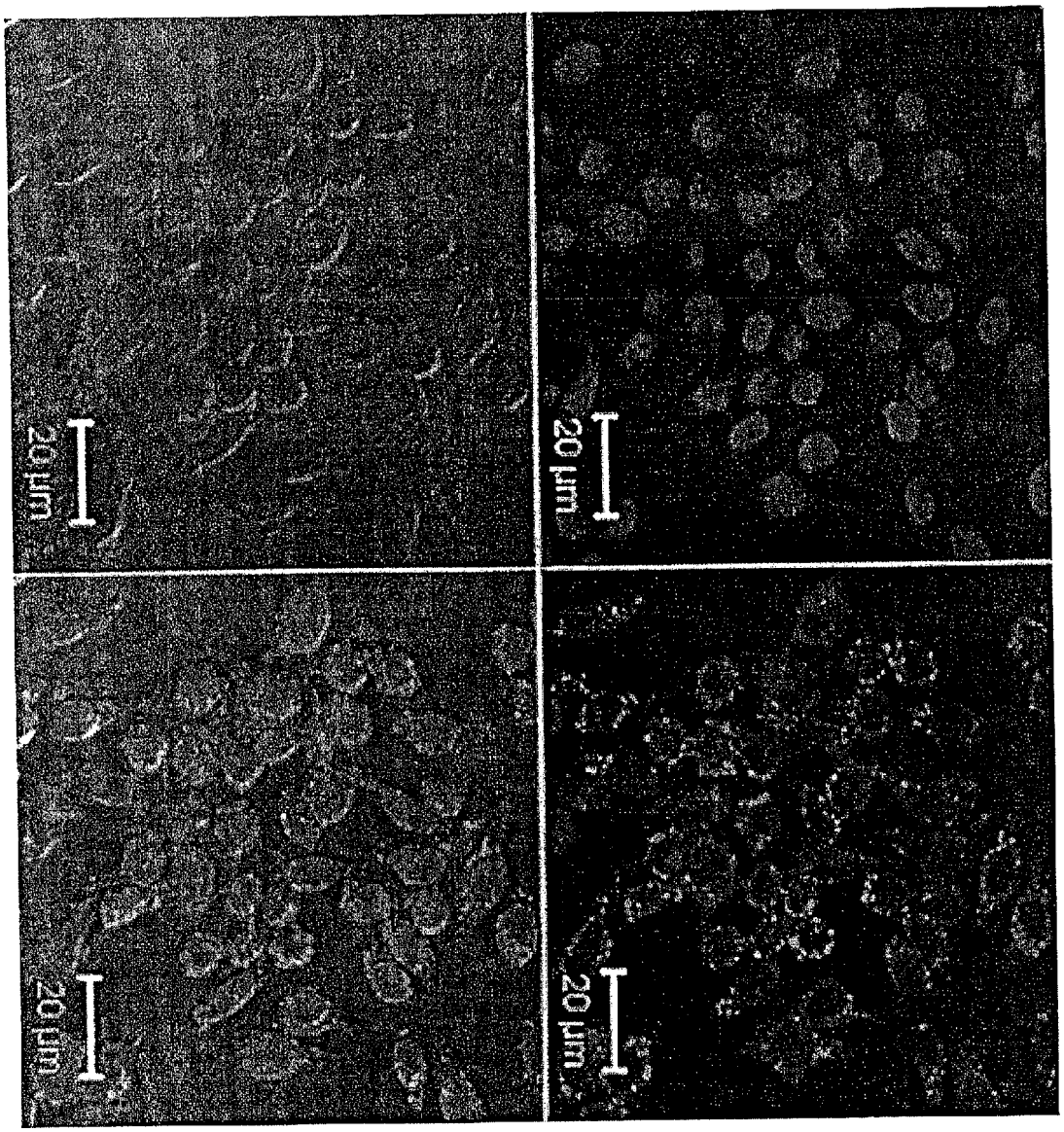
FIG. 16 shows CLSM images of RAW264.7 cells incubated with PEG-RITC-TaO$_x$ of the present invention for 24 h (Scale bar: 20 μm). The nuclei were stained blue with 4'-6-diamidino-2-phenylindole (DAPI).
Figure 17:
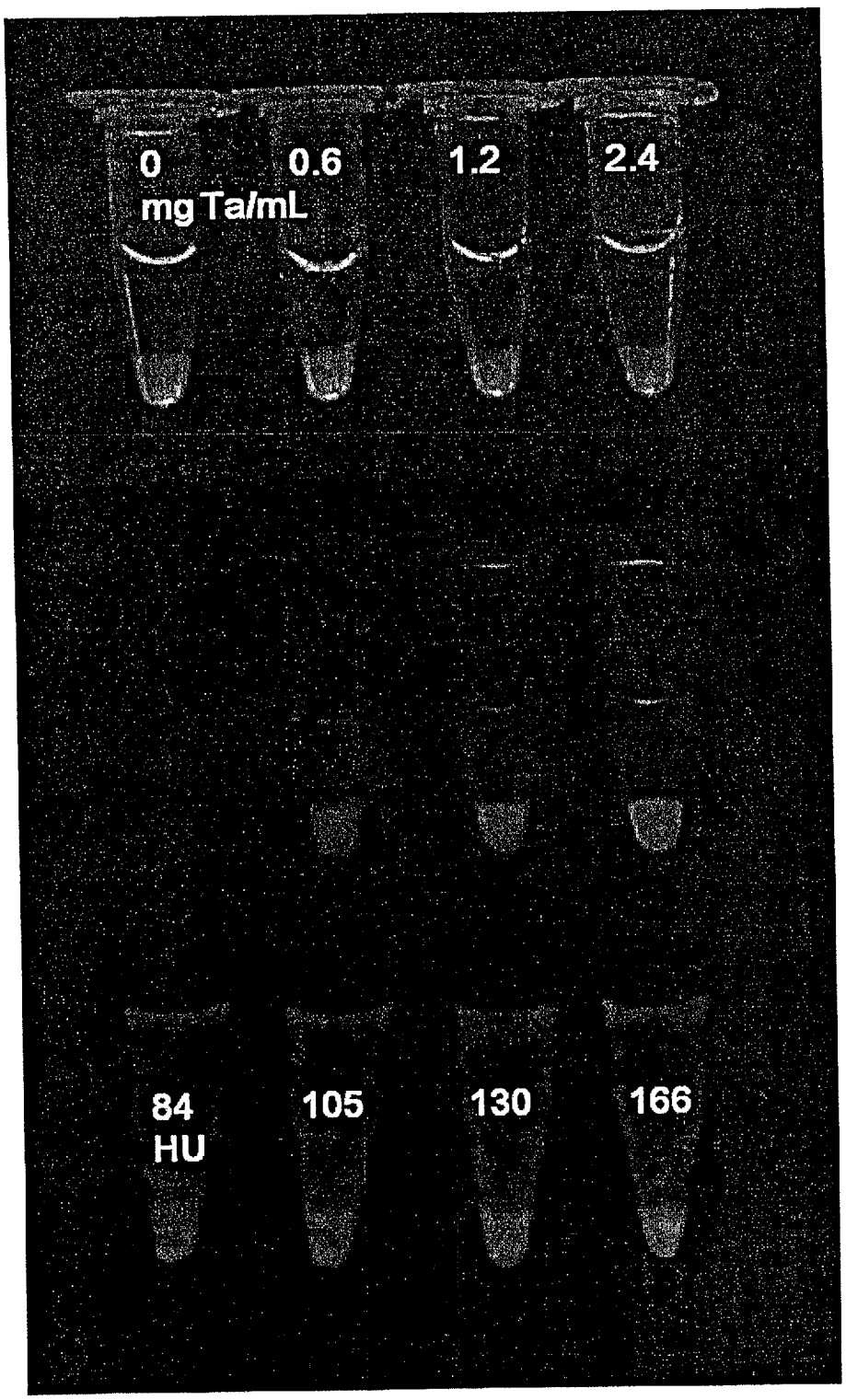
FIG. 17 shows cellular imaging results of RAW264.7 cells incubated with various concentrations of PEG-RITC-TaO$_x$ of the present invention. Bright field image (top), fluorescence image ($\lambda_{ex}$=550 nm) (middle), and X-ray CT cell phantom image (numbers indicate CT values in HU) (bottom).

X-ray CT phantom images were acquired using various concentrations of PEG-RITC-$TaO_x$ dispersed in deionized water. The CT numbers, called Hounsfield units (HU), increased linearly as the concentration of the nanoparticles increased (FIG. 14). Although the contrast enhancement of Ta atom is slightly smaller than that of Au atom in diagnostic X-ray spectra (4.302 and 5.158 $cm^2/g$, respectively, at 100 keV), the measured HU values of the $TaO_x$ nanoparticles were much higher than those of current iodine-based X-ray contrast agents. MTT assay revealed that cell viability was not hindered by PEG-RITC-$TaO_x$ up to a concentration of 2.4 mg of Ta/mL (FIG. 15), which is an extremely high concentration. Cellular X-ray CT and fluorescence imaging were conducted to demonstrate dose-dependent uptake and in vitro multimodal imaging capability of PEG-RITC-$TaO_x$. Cellular uptake was investigated by incubating murine macrophage cells (RAW264.7) with different concentrations of nanoparticles in serum-containing media. The confocal laser scanning microscopy (CLSM) images in FIG. 16 revealed that the nanoparticles were taken up by RAW264.7 cells via endocytosis. Fluorescence images of the cells after uptake of the nanoparticles show that the red luminescence became more intense and that HU values increased as the concentration increased (FIG. 17). These fluorescence and X-ray CT results demonstrated in vitro bimodal imaging capability as well as dose-dependent uptake of the $TaO_x$ nanoparticles by mammalian cells.

Figure 18:
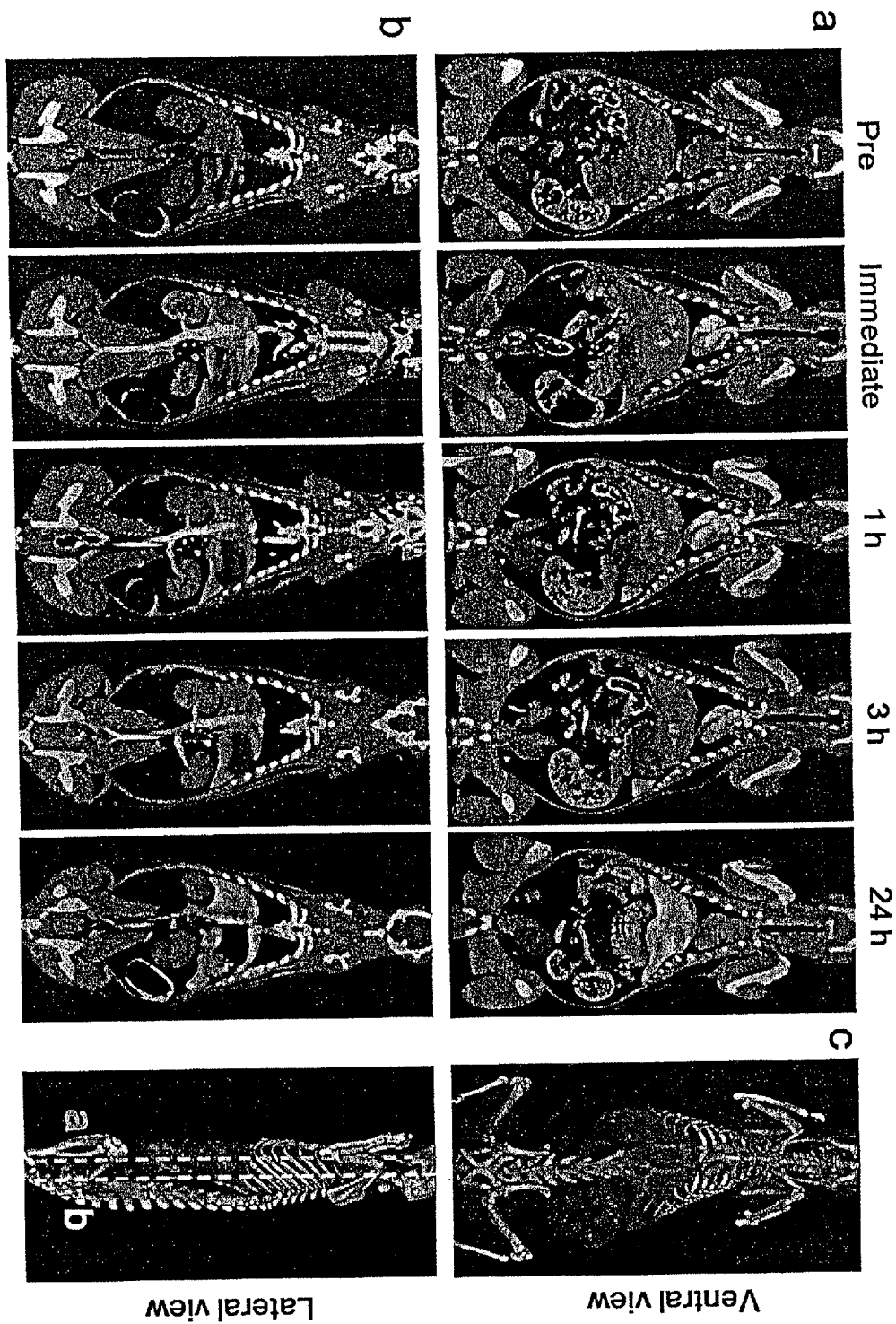
FIG. 18 shows in vivo X-ray CT imaging (a)-(b), where serial CT coronal views of a rat following injection of 1 mL of PEG-RITC-TaO$_x$ solution (840 mg/kg) into the tail vein. (a) heart and liver (coronal view cut along the yellow dotted line in (c)), (b) spleen, kidney, and inferior vena cava (coronal view cut along the white dotted line in (c)), and (c) 3D-renderings of in vivo CT images reveal the ventral (top) and lateral (bottom) side of the heart and great vessels. The images were obtained immediately after injection.

To perform in vivo X-ray CT imaging, PEG-RITC-$TaO_x$ (840 mg/kg) was injected intravenously into the tail vein of a rat. Distribution of the particles was tracked by X-ray CT imaging before injection as well as immediately, 5 min, 30 min, 1 h, 2 h, 3 h, and 24 h after injection (FIG. 18). Once the nanoparticles were injected, the vessels were preferentially enhanced, enabling spatially-described, volume-rendered images of the blood pool (FIG. 18c). The enhancement continued for over 3 h, indicating long circulation of the particles. The nanoparticles eventually were accumulated by macrophages in the spleen and liver. The HU values of the blood vessels and heart reached maximum values immediately after injection and then decreased slowly, whereas the HU values of the liver and spleen gradually increased (Table 1).

TABLE 1

| | Previous | immediate | 1 h | 3 h | 24 h |
|---|---|---|---|---|---|
| Heart | 74 | 237 | 239 | 198 | 105 |
| Liver | 84 | 110 | 124 | 130 | 191 |
| Kidney | 61 | 95 | 80 | 93 | 80 |
| Spleen | 85 | 132 | 173 | 167 | 192 |
| Inferior vena cava | 64 | 232 | 234 | 217 | 103 |

Figure 19:
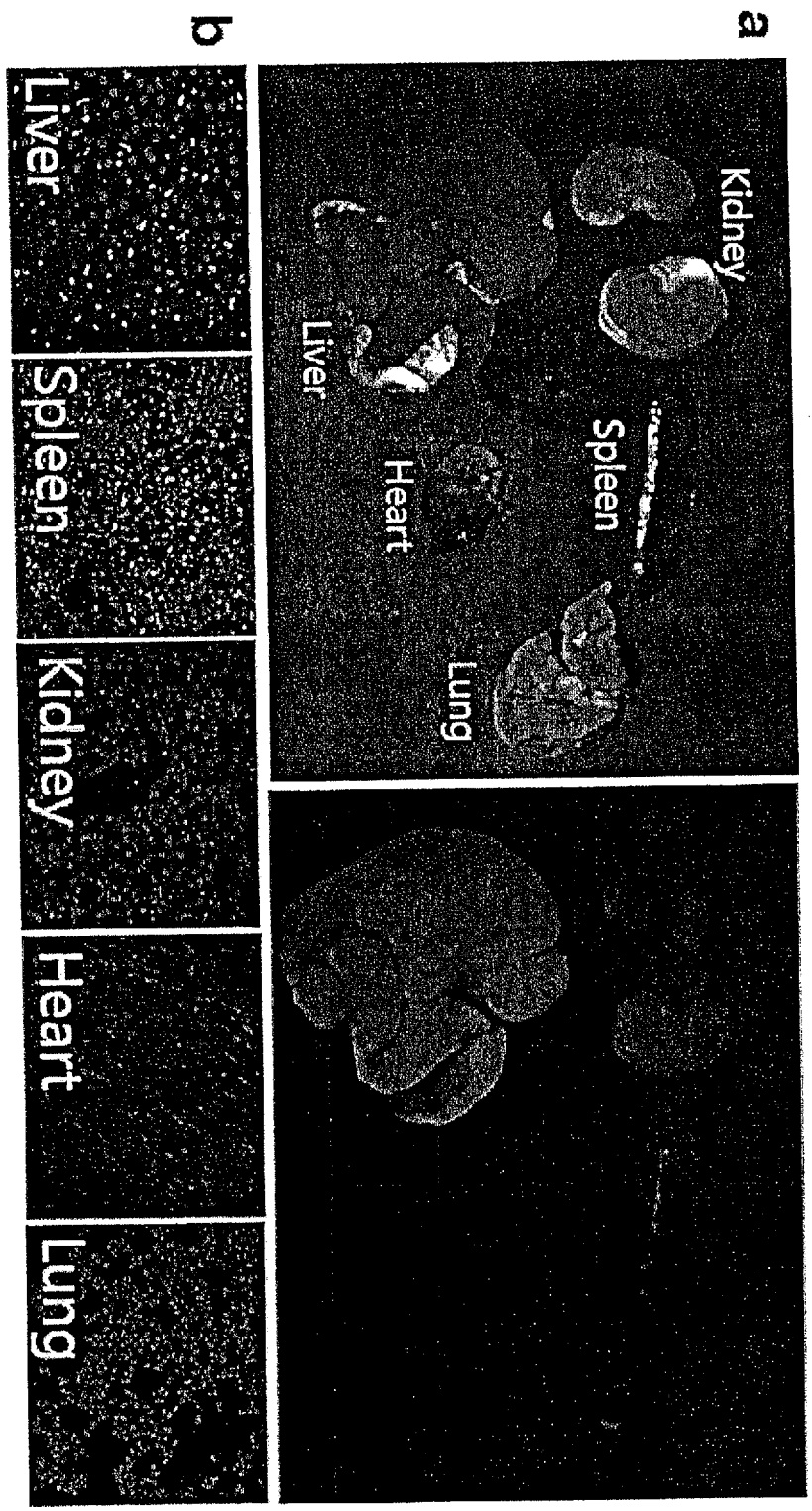
FIG. 19 illustrates biodistribution of PEG-RITC-TaO$_x$ by the fluorescence imaging of the liver, spleen, heart, kidney, and lung, harvested from the rat 24 h after intravenous injection. (a) photographic image (left) and corresponding fluorescence image (right) of the organs. (b) Confocal microscopy images of the corresponding tissue samples stained blue with 4'-6-diamidino-2-phenylindole (DAPI) showing existence of red-emitting PEG-RITC-TaO$_x$.
Figure 20:
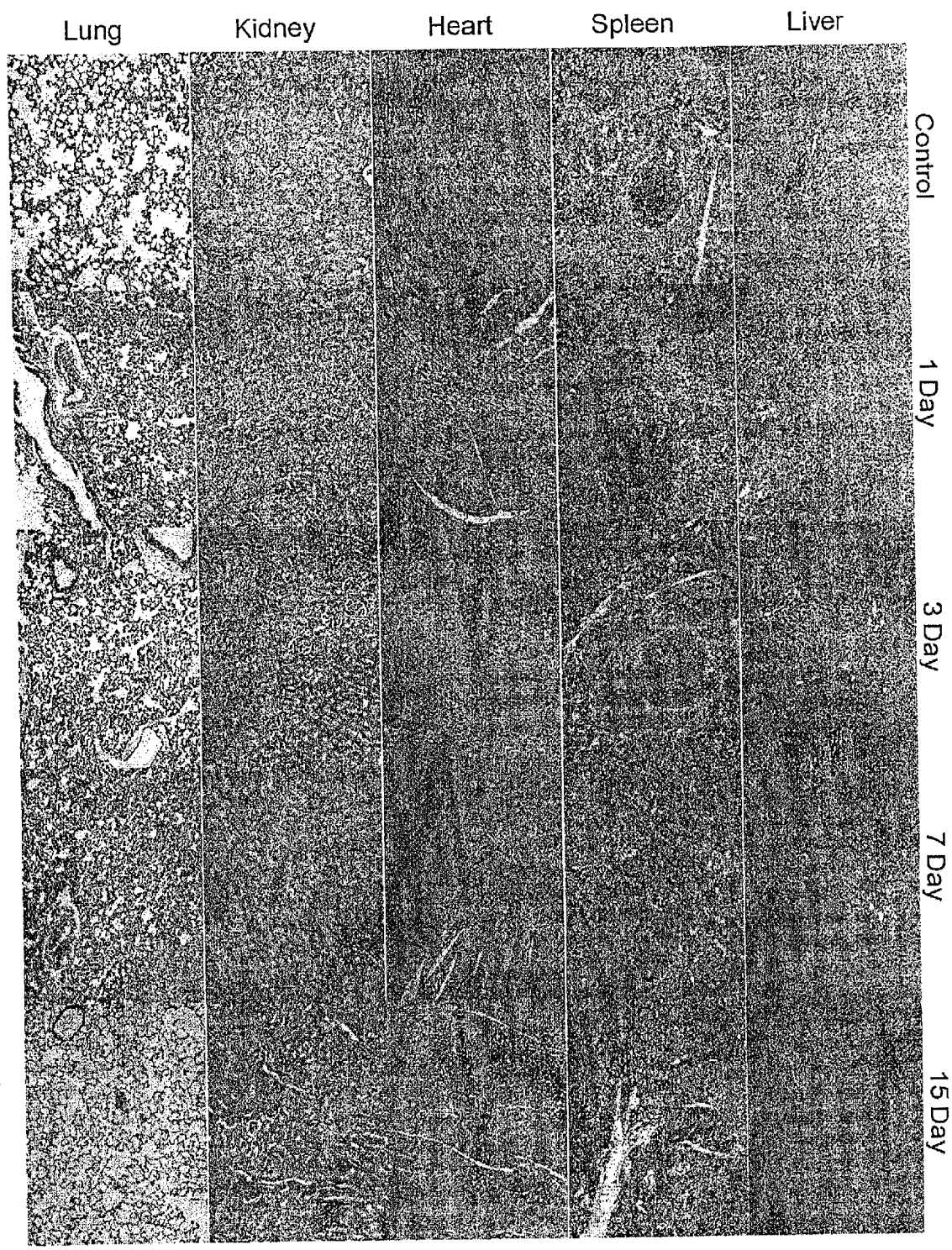
FIG. 20 shows time course of histological changes in the liver, spleen, heart, kidney, and lung of rats that received single intravenous injection of 1 mL of either PBS (control) or PEG-RITC-TaO$_x$ (840 mg/kg dose in PBS) followed by dissection at the indicated times. Sections were stained with H&E and observed under a light microscope at 100× magnification.
Figure 21:
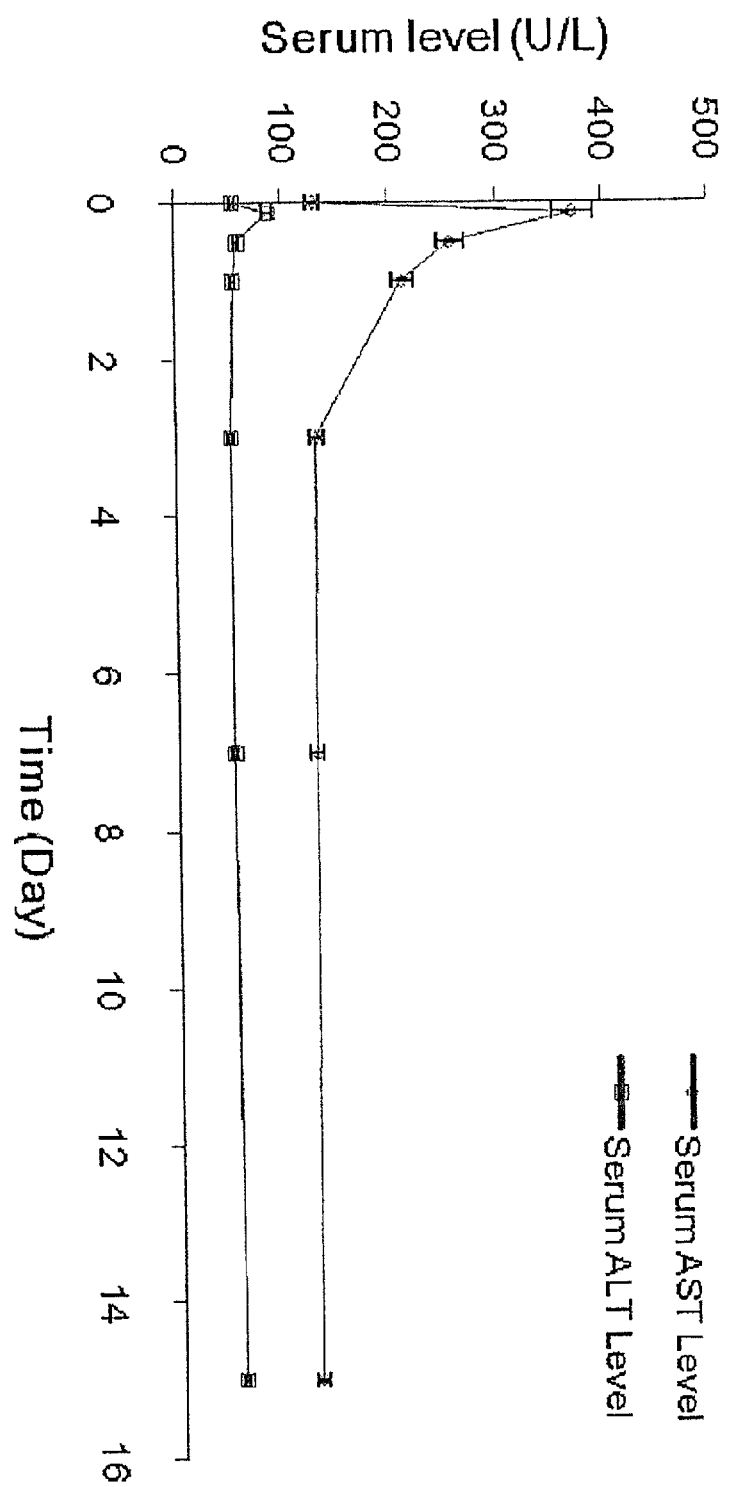
FIG. 21 shows changes in serum liver enzyme levels as a function of time. Time=0 corresponds to the moment of single intravenous injection of PEG-RITC-TaO$_x$ in rats (840 mg/kg dose in 1 mL of PBS). Blue line indicates aspartate aminotransferase (AST) and red line shows alanine aminotransferase (ALT). Data presented as mean±sem (n=4). Data at time=0 is saline control.

After 24 h of CT imaging, the rat was sacrificed, and the biodistribution of PEG-RITC-$TaO_x$ was visualized by fluorescence imaging of the dissected organs. CLSM images of the samples showed that most of the nanoparticles were found in the liver and spleen (FIG. 19). To determine whether PEG-RITC-$TaO_x$ cause any harmful effects or any diseases in these organs, long term toxicity of the nanoparticles was investigated by monitoring histological changes in several organs, including the liver, spleen, heart, kidney and lung, for more than 2 weeks. Rats were dissected at 1 day, 3 day, 7 day, and 15 day after the injection of single dose (840 mg/kg) of PEG-RITC-$TaO_x$. hematoxylin and eosin (H&E) stains of their organs showed no evidence of adverse effect of the nanoparticles (FIG. 20). Serum levels of alanine aminotransferase (ALT) and aspartate aminotransferase (AST) were also measured over time to determine the effect on liver function. The single dose injection induced transient increase of the serum level, which declined rapidly and returned to normal at day 3 (FIG. 21). These results demonstrate that tantalum oxide nanoparticles exhibit little toxicity on liver as well as other organs.

Figure 22:
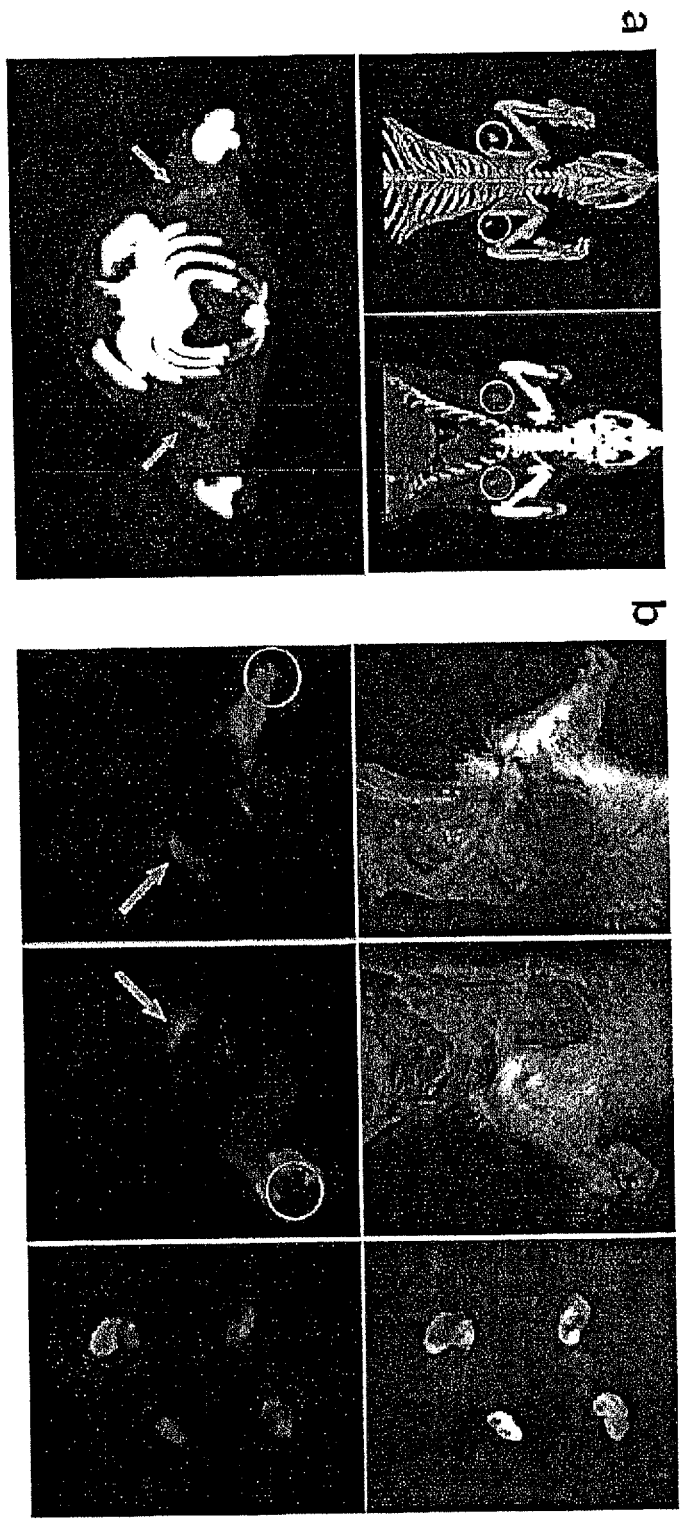
FIG. 22 shows sentinel lymph node mapping and resection, according to one embodiment of the present invention.
Figure 23:
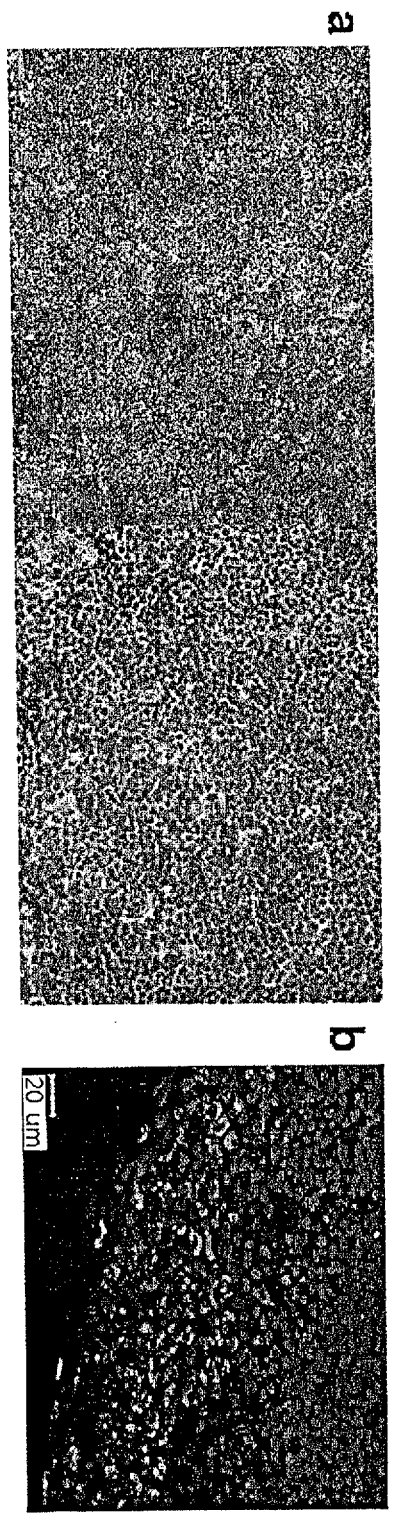
FIG. 23a shows histological section of lymph node sample dissected by the bimodal image-guided surgery. Sections were stained with H&E and observed under a light microscope at 100× (left) and 400× (right) magnification.
FIG. 23b shows confocal microscopy image of the dissected lymph node stained blue with 4'-6-diamidino-2-phenylindole (DAPI) showing existence of PEG-RITC-TaO$_x$ emitting red fluorescence.

Sentinel lymph node mapping is very important for the precise determination of tumor metastasis. By precisely mapping the lymph nodes, unnecessary dissection from surgery can be avoided. To deliver the contrast agent to sentinel lymph nodes, 100 μL of PEG-RITC-TaO$_x$ solution was intradermally injected into the rats' paws. Two hours following injection, the locations of the lymph nodes were determined by X-ray contrast enhancement (FIG. 22a). To investigate whether or not the resection of lymph nodes can be assisted by bimodal imaging, the locations of the lymph nodes were first determined using the volume-rendered CT images. Once a site was located, the area of the lymph nodes to be dissected was specified using fluorescence imaging during the operation, followed by successful extraction (FIG. 22b). In the dissected lymph nodes, nanoparticles were found by fluorescence imaging, but no histological changes were observed by H&E staining (FIG. 23).

The invention claimed is:

1. A method for preparing surface-modified tantalum oxide nanoparticles, comprising:
   (i) adding an aqueous phase to an organic solvent which contains a surfactant, to prepare a water-in-oil microemulsion;
   (ii) introducing a tantalum precursor to said microemulsion;
   (iii) adding a surface-modifier having an organic silane group or phosphine group to a solution obtained at the step (ii);
   (iv) removing said organic solvent from a product obtained at the step (iii); and
   (v) separating surface-modified tantalum oxide nanoparticles from a mixture obtained at the step (iv),
wherein said organic silane group is at least one selected from the group consisting of methacryloxypropyltrimethoxy silane (MPTMS) and 3-aminopropyltriethoxy silane (APS).

2. The method of claim 1, wherein said surfactant is a nonionic surfactant.

3. The method of claim 1, wherein said organic solvent is at least one selected from the group consisting of cyclohaxane, hexane, heptane, octane, isooctane, nonane, decane and toluene.

4. The method of claim 1, wherein said aqueous phase additionally comprises a hydrophilic solvent.

5. The method of claim 1, wherein a size of said tantalum oxide nanoparticle is controlled by changing a ratio of said water and said hydrophilic solvent.

6. The method of claim 4, wherein said hydrophilic solvent is selected from the group consisting of $C_{1-8}$ alcohol, acetonitrile, $C_{1-8}$ ether and acetone.

7. The method of claim 1, wherein said aqueous phase additionally comprises a co-surfactant.

8. The method of claim 1, wherein said aqueous phase additionally comprises an acid or a base as a catalyst.

9. The method of claim 1, wherein a pH of said aqueous phase is less than or equal to 2, or more than or equal to 13.

10. The method of claim 1, wherein said tantalum precursor is $C_{1-4}$ tantalum alkoxide or tantalum salt.

11. The method of claim 1, wherein said surface-modifier is trioctylphosphine (TOP).

12. The method of claim 1, wherein a functional substance selected from the group consisting of a biocompatible material, an organic dye, a bioactive material, a functional group, an organic molecule, an organometal, a nanoparticle, a shell structured material and combinations thereof, is attached to said surface-modifier at the opposite side to a silane or phosphine group which is attached to a surface of said nanoparticle.

13. The method of claim 12, wherein said biocompatible material is selected from the group consisting of polyvinyl alcohol, polylactide, polyglycolide, poly(lactide-co-glycolide), polyanhydride, polyester, polyetherester, polycaprolactone, polyesteramide, polyacrylate, polyurethane, polyvinyl fluoride, poly(vinyl imidazole), chlorosulphonate polyolefin, polyethylene oxide, poly(ethylene glycol), dextran, a mixture thereof, and a copolymer thereof.

14. The method of claim 12, wherein said organic dye is selected from the group consisting of rhodamine, rhodamine B isothiocyanate, fluoresceine, luciferin, and combinations thereof.

15. The method of claim 12, wherein said bioactive material is selected from the group consisting of a target-specific material selected from the group consisting of a protein, RNA, DNA, an antibody and combinations thereof, which attaches specifically to an in vivo targeted material; an apoptosis-inducing gene or a toxic protein; a fluorescent material; an isotope; a material responsive to a light, an electromagnetic wave, or heat; a pharmacologically active material; and combinations thereof.

16. The method of claim 1, wherein the step (iv) is carried out by heating said organic solvent less than or equal to 60° C.

17. The method of claim 1, wherein said method for preparing surface-modified tantalum oxide nanoparticles is carried out in a single reactor.

18. A surface-modified tantalum oxide nanoparticle comprising a tantalum oxide nanoparticle, and a functional material attached to said tantalum oxide nanoparticle through a phosphine group or a silane group, wherein said silane group is at least one selected from the group consisting of methacryloxypropyltrimethoxy silane (MPTMS) and 3-aminopropyltriethoxy silane (APS).

19. The surface-modified tantalum oxide nanoparticle of claim 18, wherein said functional material is selected from the group consisting of a biocompatible material, an organic dye, a bioactive material, a functional group, an organic molecule, an organometal, a nanoparticle, a shell structured material and combinations thereof.

20. The surface-modified tantalum oxide nanoparticle of claim 18, wherein a size of surface-modified tantalum oxide nanoparticle is 3 nm to 50 nm.

21. The surface-modified tantalum oxide nanoparticle of claim 18, wherein said tantalum oxide is TaO.

22. A contrast agent for X-ray computed tomography comprising a tantalum oxide nanoparticle, and a functional substance which is attached to said tantalum oxide nanoparticle through a phosphine or silane group, wherein said silane group is at least one selected from the group consisting of methacryloxypropyltrimethoxy silane (MPTMS) and 3-aminopropyl-triethoxy silane (APS).

23. The contrast agent of claim 22, wherein said functional substance is selected from the group consisting of polyvinyl alcohol, polylactide, polyglycolide, poly (lactide-co-glycolide), polyanhydride, polyester, polyetherester, polycaprolactone, polyesteramide, polyacrylate, polyurethane, polyvinyl fluoride, poly(vinyl imidazole), chlorosulphonate polyolefin, polyethylene oxide, poly(ethylene glycol), dextran, a mixture thereof, and a copolymer thereof.

24. The contrast agent of claim 22, further comprising an organic dye which is attached to the surface of said tantalum oxide nanoparticle through a phosphine or silane group.

25. The contrast agent of claim 24, wherein said organic dye is selected from the group consisting of rhodamine, rhodamine B isothiocyanate, fluoresceine, luciferin, and combinations thereof.

26. The contrast agent of claim 22, further comprising a bioactive material which is attached to the surface of said tantalum oxide nanoparticle through a phosphine or silane group.

27. The contrast agent of claim 26, wherein said bioactive material is selected from the group consisting of a target-specific material selected from the group consisting of a protein, RNA, DNA, an antibody and combinations thereof, which attaches specifically to an in vivo targeted material; an apoptosis-inducing gene or a toxic protein; a fluorescent material; an isotope; a material responsive to a light, an electromagnetic wave, or heat; a pharmacologically active material; and combinations thereof.

28. The contrast agent of claim 22, wherein said tantalum oxide is TaO.

29. A method for preparing a surface-modified tantalum oxide nanoparticle/polymer nanocomposition, comprising:
(i) adding an aqueous phase to an organic solvent which contains a surfactant, to prepare a water-in-oil microemulsion;
(ii) introducing a tantalum precursor to said microemulsion;
(iii) adding a surface-modifier having an organic silane group or phosphine group to a solution obtained at the step (ii);
(iv) removing said organic solvent from a product obtained at the step (iii);
(v) separating surface-modified tantalum oxide nanoparticles from a mixture obtained at the step (iv); and
(vi) adding said surface-modified tantalum oxide nanoparticle to a solution containing a polymer, followed by heating the thus obtained mixture to remove said solvent,
wherein said organic silane group is at least one selected from the group consisting of methacryloxypropyltrimethoxy silane (MPTMS) and 3-aminopropyltriethoxy silane (APS).

30. The method of claim 29, wherein said polymer is selected from the group consisting of a polyurethane copolymer, a cellulose derivative, poly(methyl methacrylate) (PMMA), poly(methyl acrylate) (PMA), a polyacryl copolymer, poly(vinyl acetate) (PVAc), a poly(vinyl acetate) copolymer, poly(vinyl alcohol) (PVA), poly(furfuryl alcohol) (PFA), polystyrene, a polystyrene copolymer, poly(ethylene oxide) (PEO), poly(propylene oxide) (PPO), a poly(ethylene oxide) copolymer, polycarbonate (PC), poly(vinyl chloride) (PVC), polycaprolactone, poly(vinyl pyrrolidone) (PVP), poly(vinyl fluoride), poly(vinylidene fluoride), polyimide, poly(ethylene terephthalate) and combinations thereof.

31. The method of claim 29, wherein said aqueous phase further comprises a hydrophilic solvent.

32. The method of claim 31, wherein said hydrophilic solvent is selected from the group consisting of $C_{1-8}$ alcohol, acetonitrile, $C_{1-8}$ ether and acetone.

33. A film prepared by a method comprising applying the surface-modified tantalum oxide nanoparticle/polymer nanocomposition produced by the method of claim 29 on a substrate.

* * * * *